United States Patent [19]

Russell et al.

[11] Patent Number: 4,506,678

[45] Date of Patent: Mar. 26, 1985

[54] PATIENT MONITOR FOR PROVIDING RESPIRATION AND ELECTROCARDIOGRAM SIGNALS

[75] Inventors: Donald J. Russell, Kennessaw; Michael A. Sanders, Woodstock, both of Ga.

[73] Assignee: Healthdyne, Inc., Marietta, Ga.

[21] Appl. No.: 396,837

[22] Filed: Jul. 9, 1982

Related U.S. Application Data

[63] Continuation-in-part of Ser. No. 386,187, Jun. 7, 1982.

[51] Int. Cl.³ .............................................. A61B 5/04
[52] U.S. Cl. ..................................... 128/723; 128/630; 128/696
[58] Field of Search ............... 128/670, 671, 695, 696, 128/708, 716, 723, 902, 908

[56] References Cited

U.S. PATENT DOCUMENTS

| | | | |
|---|---|---|---|
| 3,488,586 | 1/1970 | Watrous | 324/96 |
| 3,510,765 | 5/1970 | Baessler | 128/696 |
| 3,545,429 | 12/1970 | Pelta et al. | 128/723 |
| 3,572,317 | 3/1971 | Wade | 128/671 |
| 3,579,138 | 5/1971 | Harris | 330/86 |
| 3,580,243 | 5/1971 | Johnson | 128/696 |
| 3,581,219 | 5/1971 | Alexander | 128/696 |
| 3,587,562 | 6/1971 | Williams | 128/696 |
| 3,602,215 | 8/1971 | Parnell | 128/696 |
| 3,794,841 | 2/1974 | Cosentino et al. | 455/602 |
| 3,910,257 | 10/1975 | Fletcher et al. | 128/908 |
| 3,922,686 | 10/1975 | France et al. | 346/33 ME |
| 3,927,663 | 12/1975 | Russell et al. | 128/702 |
| 3,937,214 | 2/1976 | Hutchins | 194/63 |
| 3,938,051 | 2/1976 | Eisenberg | 128/695 |
| 3,986,495 | 10/1976 | Miller | 128/696 |
| 4,068,669 | 1/1978 | Niemi | 128/908 |
| 4,129,125 | 12/1978 | Lester et al. | 128/671 |
| 4,193,393 | 3/1980 | Schlager | 128/2.06 A |
| 4,232,682 | 11/1980 | Veth | 128/671 |
| 4,248,240 | 3/1981 | Van Eykern | 128/671 |
| 4,270,547 | 6/1981 | Steffen et al. | 128/671 |
| 4,289,142 | 9/1981 | Kearns | 128/723 |
| 4,306,567 | 12/1981 | Krasner | 128/671 |
| 4,318,110 | 3/1982 | Iino et al. | 346/32 |

Primary Examiner—William E. Kamm
Assistant Examiner—Max F. Hindenburg
Attorney, Agent, or Firm—Schwartz, Jeffery, Schwaab, Mack, Blumenthal & Koch

[57] ABSTRACT

The patient monitor includes a patient unit having a probe connected to receive a carrier signal, which probe is adapted for connection to the body of a patient to be monitored. The carrier signal is passed through the patient's body and modulated in accordance with the respirations of the patient to produce a modulated carrier signal. A carrier detection circuit is connected to receive the modulated carrier signal and produce a demodulated respiration signal. An ECG circuit also receives the carrier signal and filters out ECG signals. The respiration and ECG signals are passed to an analysis unit. Both the patient unit and analysis unit contain baseline correction circuits for maintaining a predetermined baseline.

52 Claims, 12 Drawing Figures

FIG. 2

PATIENT MONITOR FOR PROVIDING RESPIRATION AND ELECTROCARDIOGRAM SIGNALS

CROSS REFERENCE TO RELATED APPLICATIONS

This is a continuation-in-part of U.S. application Ser. No. 386,187, filed June 7, 1982.

BACKGROUND OF THE INVENTION

1. Field of the Invention

This invention relates to systems for monitoring specific patient parameters and more particularly to systems which monitor electrocardiogram (ECG) waveforms and respiration waveforms, and which are designed to provide output signals which have a controlled amplitude and baseline.

2. Discussion of Related Art

Monitoring of specific patient parameters on a continuing basis is becoming a generally accepted diagnostic tool. This is particularly true in the case of infants which are deemed "at risk" and susceptible to sudden infant death syndrome. Such infants exhibit prolonged apnea and bradycardia episodes. Apnea is defined as the cessation of respiration, and bradycardia is defined as low heart rate A presently available monitor is a Model 16000 Infant Monitor manufactured and sold by Healthdyne, Inc., of Marietta, Ga. This infant monitor is designed to manage infants who have been determined to be at risk by providing signals indicative of the infant's respiration and heart activity. The monitor contains two control adjustments which must be made by the operator to properly set up the unit. These controls are for the sensitivity setting of the respiration and ECG channels. The monitor provides excellent operation when the sensitivity settings are proper. However, it is possible for people to poorly adjust the sensitivity settings and in so doing cause signal dropouts and accompanying false alarms. Accordingly, a need has developed for a monitor which automatically controls the sensitivity of the respiration and ECG signals.

The present invention can be used in combination with a recorder to provide a visual display of the monitored parameters. Such a recorder is disclosed in U.S. application Ser. No. 383,296, filed May 28, 1982, and in a continuation-in-part of Ser. No. 383,296, which applications are incorporated by reference herein.

SUMMARY OF THE INVENTION

One object of the present invention is to provide a patient monitor which produces respiration and ECG output signals that are indicative of the patient's respiration and heart activity, respectively.

Another object of the present invention is to provide a patient monitor which includes a patient connected unit which receives respiration and ECG signals from a patient, and a signal analysis unit which receives the respiration and ECG signals from the patient connected unit, but in which the patient connected unit and signal analysis unit are electrically isolated from each other in order to eliminate the possibility of electrical shock to the patient due to malfunctioning of the signal analysis unit.

Another object of the present invention is to provide a patient monitor having a patient connected unit and a signal analysis unit in which the patient connected unit maintains a proper baseline for received signals, and in which the signal analysis unit can control the baseline correction function of the patient connected unit.

Another object of the present invention is to provide a patient monitor which has a patient connected unit which is capable of sensing the existence of a loose lead on the patient and eliminating an output from the patient connected unit during the presence of a loose lead.

A further object of the present invention is to provide a patient monitor in which signals are transmitted from a patient connected unit to a signal analysis unit in a manner which eliminates the possibility of signal distortion due to interference by spurious signals.

Yet another object of the present invention is to provide a patient monitor having a signal analysis unit which can detect a deviation of a signal from a proper baseline at several points in the unit.

A further object of the present invention is to provide a patient monitor which includes an ECG channel in which the gain of the ECG signal is controlled automatically.

A still further object of the present invention is to provide a patient monitor having a signal analysis unit in which the baseline of a signal can be restored automatically at a controlled rate.

In accordance with the above and other objects, the patient monitor of the present invention comprises a patient unit having a probe connected to receive a carrier signal, which probe is adapted for connection to the body of a patient to be monitored, whereby the carrier signal is passed through the patient's body and modulated in accordance with respirations of the patient to produce a modulated carrier signal. A carrier detection circuit is connected to receive the modulated carrier signal and produce a demodulated respiration signal. An amplifier amplifies the demodulated respiration signal and the resultant amplified respiration signal pulse width modulates (PWM) an oscillator to produce PWM respiration signal.

The patient monitor also includes an analysis unit which contains a carrier generation circuit for producing the carrier signal. The analysis unit also contains a pulse width demodulation circuit which receives the PWM respiration signal, demodulates the signal, and thereby produces a respiration data signal. An output circuit of the analysis unit is connected to receive the respiration data signal, amplify and level shift the respiration data signal and output the resultant respiration data signal.

The monitor also includes isolation circuitry for electrically isolating the patient unit from the analysis unit.

The patient unit also includes a baseline correction circuit for sensing the DC level of the demodulated respiration signal and adding or subtracting a DC signal to the demodulated respiration signal in response to the sensed DC level. The base line correction circuit includes a capacitor which is charged in response to the sensed DC level. The patient monitor also includes a circuit for changing the charging rate of the capacitor when the DC level of the respiration data signal reaches a predetermined amount. This charging rate circuit comprises a circuit contained in the analysis unit for deactivating the carrier generation circuit to stop the production of the carrier signal, and a circuit in the patient unit for sensing the lack of carrier signal and reducing the charging time constant of the capacitor in response thereto.

The analysis unit also includes a baseline correction circuit for sensing the DC level of the respiration data signal and adding or subtracting a DC signal to the respiration data signal in response to the sensed DC level. The analysis unit baseline correction circuit includes a capacitor which is charged in accordance with the sensed DC level and includes circuitry for varying the rate of charging of the capacitor. The circuit for varying the rate of charging the capacitor includes a circuit for reducing the charging time constant of the capacitor when the DC level of the respiration data signal is above or below predetermined limits. This rapid charge circuitry includes a programmed microprocessor, and a pair of comparator circuits connected to receive the respiration data signal and produce outputs when the respiration data signal is above or below upper and lower limits, respectively.

The patient monitor also includes an ECG sensing circuit which includes a filter contained in the patient unit for passing frequencies associated with an ECG signal. The ECG circuit also includes an amplifier for amplifying the frequencies passed by the filter to produce an amplified ECG signal, and a frequency modulation circuit connected to frequency modulate the amplified ECG signal to produce a PWM ECG signal. The amplifier and frequency modulation circuit are contained in the patient unit, and a frequency demodulation circuit is contained in the analysis unit for demodulating the PWM ECG signal to produce an ECG data signal. An ECG output circuit is contained in the analysis unit for receiving the ECG data signal, amplifying, level shifting and outputting that signal.

The ECG output circuit includes an automatic gain control circuit for controlling the amplitude of the ECG data signal to within predetermined limits. The automatic gain control circuit includes a gain controllable amplifier in the form of an operational amplifier with a variable resistance optical coupler contained in a feedback loop, and a gain control circuit in the form of an integrator circuit having an input connected to the output of the gain controllable amplifier and having an output connected to the control input of the optical coupler.

The monitor also includes an ECG baseline correction circuit in the patient unit for sensing the DC level of the amplified ECG signal and adding or subtracting a DC signal to the amplified ECG signal in response to this sensed DC level. The ECG baseline correction circuit includes a capacitor which is charged in accordance with the sensed DC level.

The charging time constant of capacitor of the ECG baseline circuit varied in a manner similar to the variation of the charging time constant of the capacitor in the respiration baseline correction circuit of the patient unit. That is, when the DC level of the respiration data signal reaches a predetermined level, the carrier generation circuit is deactivated thus stopping the generation of the carrier signal. A circuit in the patient unit senses the cessation of the carrier signal and reduces the charging time constants of the capacitors in both the ECG baseline correction circuit and the respiration baseline correction circuit. The carrier generation circuit is similarly deactivated due to a high DC level of the ECG data signal.

BRIEF DESCRIPTION OF THE DRAWINGS

The above and other objects of the invention will become more readily apparent when the invention is more fully described below, reference being had to the accompanying drawings in which like reference numerals represent like parts throughout, and in which:

FIG. 2 is a schematic diagram showing the patient unit of the present invention;

DETAILED DESCRIPTION OF THE PREFERRED EMBODIMENT

Figure 1:
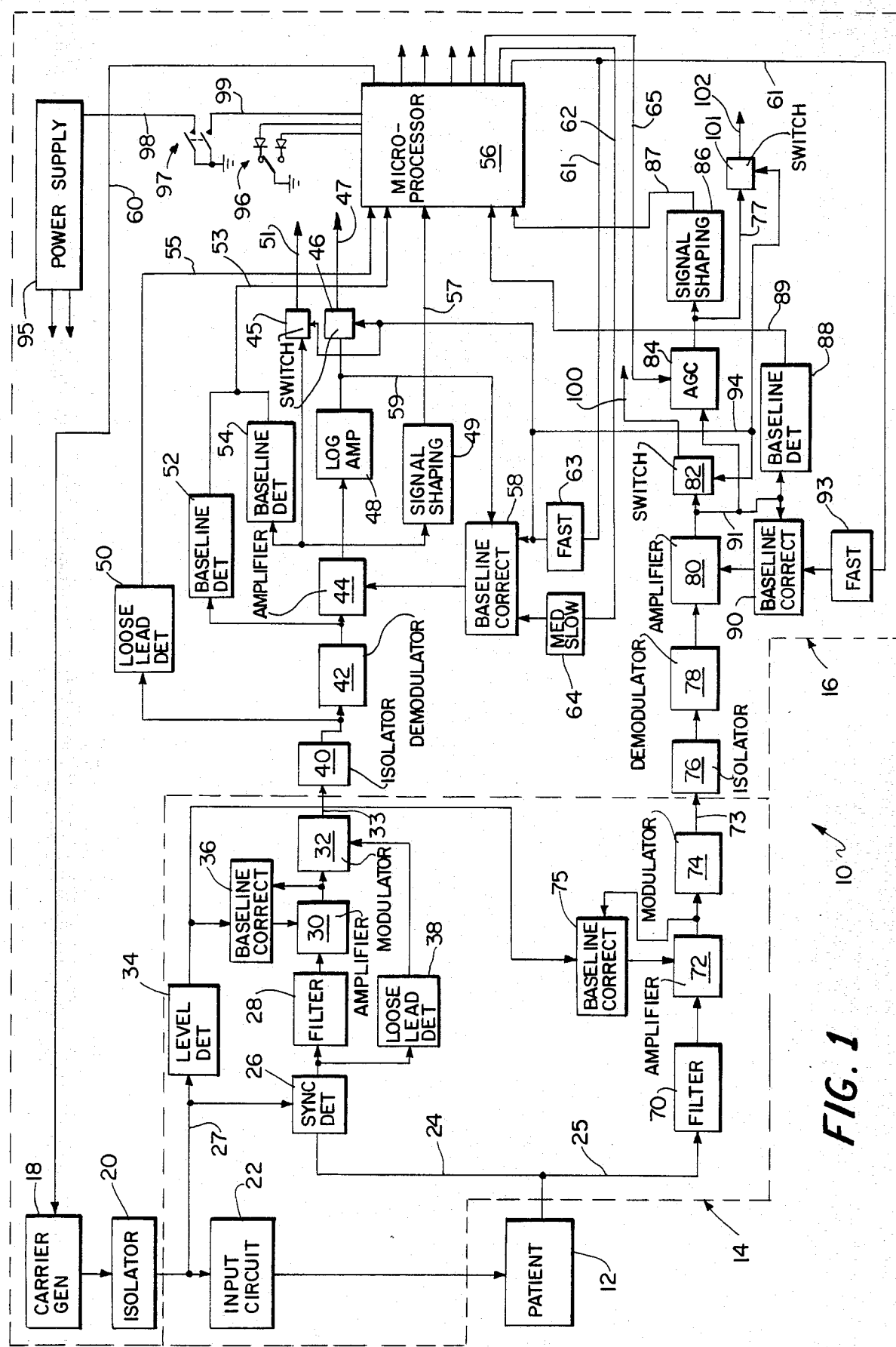
FIG. 1 is a block diagram of the patient monitor of the present invention.

FIG. 1 shows a block diagram of the patient monitor 10 of the present invention. Patient monitor 10 is connected to a patient 12 for the purpose of providing electrocardiogram signals indicative of the patient's heart activity and respiration signals indicative of the patient's respiration. The signals provided by the patient monitor 10 can be used to actuate alarms indicating bradycardia or apnea episodes, can be displayed on any convenient device such as a CRT, and can be recorded for future reference to assist a physician to make a diagnosis of the patient.

Monitor 10 includes a patient unit 14 which contains all patient connected leads. Signals developed in patient unit 14 are transmitted to signal analysis unit 16 which performs control and analysis functions for the monitor. Also, analysis unit 16 contains the monitor power supply. In order to guard against electrical shock to patient 12, low voltage levels are used in patient unit 14 and patient unit 14 is electrically isolated from analysis unit 16 so that circuit malfunctions in the analysis unit will not result in electrical shocks to the patient.

Carrier generator 18 is located in the analysis unit and produces a high frequency carrier signal. This carrier signal can be approximately 100 khz. This carrier signal is passed to patient unit 14 through an isolation transformer 20. In patient unit 14, the voltage and current levels of the carrier signal are adjusted in input circuit 22 and passed to patient 12 through standard carbon or silver chloride electrodes. The carrier signal is modulated in a known manner according to an increase or decrease in the chest expansion of the patient so as to produce an amplitude modulated signal in which the envelope indicates respiration of the patient. Also, the normal voltages associated with heart activity of the patient are added to this signal. The resultant signal is passed through line 24 to the respiration channel of the monitor, and through line 25 to the ECG channel of the monitor.

Input circuit 22 also includes power supply circuitry which receives the carrier signal and rectifies and filters this signal to produce a low level bias voltage for the patient unit 14.

The respiration channel includes a synchronous detector 26 which receives the carrier signal on line 27 and synchronously detects the amplitude modulated carrier signal received on line 24. The detected signal is low pass filtered in filter 28 and the demodulated respiration signal is passed to amplifier 30. The demodulated respiration signal is amplified in amplifier 30 and the amplified respiration signal is passed to modulator 32. Modulator 32 is a pulse width modulator in the form of a voltage controlled oscillator which converts the amplified respiration signal into a pulse width modulated respiration signal. This pulse width modulated respiration signal is passed to isolation device 40 and then to demodulation circuit 42 of the analysis unit 16. The signal is pulse width modulated so that variations in amplitude of the signal due to, for example, spurious noise, 60 hz signals from the power supply, etc., will not affect the respiration signal adversely. The output of demodulator 42 is a respiration data signal which is passed to amplifier 44. From amplifier 44, the signal is passed to logarithmic amplifier 48 in which the dynamic range of the signal is compressed and passed through switch 46 to output line 47 which can be connected to a recorder, CRT display device, or the like. A non-compressed, linear output is taken from amplifier 44 through switch 45 and provided on output line 51 for the same purpose. The output of amplifier 44 is also passed to signal shaping circuit 49 which can be a zero crossing detector. The output of signal shaping circuit 49 is passed through line 57 to microprocessor 56, and can also be passed to an end use device such as a strip chart recorder or cathode ray tube display. Microprocessor 56 receives the signals on line 57 and can be programmed to perform standard operations such as actuating an alarm in the event of an apnea episode.

Patient unit 14 also includes a loose lead detector 38 which senses the output of synchronous detector 26. If no output is sensed from synchronous detector 26, this is interpreted as indicating that a lead has pulled loose from patient 12 and loose lead detector 38 passes an inhibit signal to modulator 32 to deactivate the modulator so that no signal will be passed to analysis unit 16. Analysis unit 16 also contains a loose lead detector 50 which senses the output from isolation circuit 40. If no output is sensed, loose lead detector 50 sends a signal through line 55 to microprocessor 56 which may sound an audible alarm, illuminate a visible alarm, or the like.

Patient unit 14 also contains a baseline correction circuit 36 which senses the DC level of the output of amplifier 30 and either adds or subtracts a DC signal via amplifier 30 to the respiration signal depending on the sensed level. If the DC offset of the respiration signal due to, for example, large signal levels due to defibrillation of the patient, or the like, reaches a limit which cannot be quickly corrected by baseline correction circuit 36, the larger DC level is passed through isolation device 40 and demodulator 42 and detected by baseline detection circuit 52. Baseline detection circuit 52 sends a signal through line 53 to microprocessor 56 which, in response to this signal, stops the operation of carrier generator 18 through line 60. Patient unit 14 has a level detecting circuit 34 which is connected to the output of isolation transformer 20. When the carrier signal is stopped by microprocessor 56, level detector circuit 34 no longer sees an output signal from isolation transformer 20 and reduces the time constant of baseline correction circuit 36 in response. Circuit 36 then rapidly corrects the baseline deviation.

Analysis unit 16 contains a baseline correction circuit 58 which receives the output of logarithmic amplifier 48 on line 59. Baseline correction circuit 58 senses the DC level of the logarithmically converted signal and adds or subtracts a DC signal to the respiration data signal in amplifier 44 based on the sensed DC level of the logarithmically converted signal. If the DC offset of the respiration data signal becomes too great for base line correction circuit 58 to compensate for, the DC level will reach a threshold set by baseline detection circuit 54 which receives the output of amplifier 44. Baseline detection circuit 54 sends a signal to microprocessor 56 which can control the baseline correction circuit action through line 61 and fast correction circuit 63 or line 62 and slow correction circuit 64. Fast and slow correction circuits 63 and 64 control the rate at which baseline correction circuit 58 follows the output of logarithmic amplifier 48. Also, microprocessor 56 can stop the carrier generation, if necessary.

The ECG channel comprises a filter 70 which passes signals in the frequency range associated with ECG signals and filters out the carrier signal. The filtered ECG signal is amplified in amplifier 72 and passed to pulse width modulation circuit 74. The amplified ECG signal is modulated in circuit 74 and passed through line 73 to isolation circuit 76 and demodulation circuit 78 of the analysis unit 16. The ECG signal is pulse width modulated in order to avoid contamination from noise. The signal is demodulated in circuit 78 and amplified in amplifier 80. The amplified signal is passed to automatic gain control circuit 84 and through switch 82 to output line 100. Automatic gain control circuit 84 maintains the amplitude of the ECG data signal within predetermined limits and passes the signal to shaping circuit 86. Shaping circuit 86 contains a filter to pass the R wave portion of the ECG signal to microprocessor 56 through line 87. If microprocessor 56 sees that the signal on line 87 is missing, it injects current through line 65 to automatic gain control circuit 84 to rapidly increase the gain of that circuit to its maximum in an attempt to restore a proper signal level.

The gain control signal is also passed through line 77 and switch 101 to line 102.

The ECG channel of patient unit 14 contains a baseline correction circuit 75 for the ECG signal. Baseline correction circuit 75 senses the output of amplifier 72 and adds or subtracts a DC signal to the ECG signal to compensate for DC drift. If the DC drift becomes too great for baseline correction circuit 75 to rapidly correct, the excessive DC level is passed through isolation circuit 76, demodulation circuit 78 and amplifier 80. Baseline detection circuit 88 receives the signal from amplifier 80 and senses that the DC level of the signal is above or below predetermined limits. Baseline detection circuit 88 sends a signal through line 89 to microprocessor 56 which in turn deactivates carrier generator 18. This causes level detection circuit 34 to reduce the time constant of baseline correction circuit 75, which then rapidly corrects the baseline deviation.

The analysis unit 16 contains a baseline correction circuit 90 which also receives the output of amplifier 80 and adjusts the baseline of the ECG signal by subtracting or adding a DC signal to the ECG data signal at amplifier 80 in response to the DC level of the ECG data signal. If baseline correction circuit 90 cannot compensate for the DC level of the ECG data signal, baseline detection circuit 88 will note an excessive baseline deviation and notify microprocessor 56 which, through line 62 and fast baseline circuit 93, reduces the time constant of baseline correction circuit 90.

In operation, carrier generator 18 passes a 100 khz carrier through isolation transformer 20 to patient unit 14. This signal is received in input circuit 22 which rectifies the signal to provide biasing voltages for the circuitry of the patient unit. Input circuit 22 also adjusts the voltage level of the carrier signal and controls the carrier signal current before passing the carrier signal to patient 12. The carrier signal is amplitude modulated in accordance with respirations of patient 12 and passed through line 24 to synchronous detector 26. The amplitude modulated respiration signal is detected and filtered in circuit 28. The filtered signal is amplified in amplifier 30 which also corrects the base line of the signal so that the DC level remains at zero volts. The signal from amplifier 30 is modulated by frequency modulation circuit 32. In the event that no signal is emitted from synchronous detector 26, loose lead detector 38 disables modulator 32. Accordingly, modulator circuit 32 does not transmit a signal through isolation circuit 40, and loose lead detector 54 therefore signals microprocessor 56 of the existence of a loose lead. Microprocessor 56 can then provide an appropriate alarm signal.

Assuming that a proper signal is passed through synchronous detector 26, if the DC level of the signal is too high or too low, this DC level is corrected by baseline correction circuit 36 in amplifier 30. Consequently, the signal passed to modulation circuit 32 should have a zero volt DC offset and should be amplified so that contamination due to noise will be minimized. This signal is pulse width modulated prior to being passed to the signal analysis unit 16, thereby further reducing the possibility of noise contamination. The signal is demodulated in circuit 42. Baseline correction circuit 36 is quite effective in compensating for offset voltages due to capacitive absorption or capacitive voltage buildup due to minor perturbations in the received signal. However, if the capacitive buildup becomes excessive due to, for example, defibrillation of the patient, the baseline must be corrected more rapidly. Accordingly, baseline detection circuit 52 senses the excessive baseline and signals microprocessor 56 to turn off carrier generator 18. Thus, the carrier wave input to patient unit 14 is removed. As a consequence, detector 34 senses the cessation of the carrier wave and reduces the time constant of baseline correction circuit 36, which rapidly corrects the baseline.

At the same time, the ECG voltage from the patient is passed along line 25 through filter 70 to amplifier 72 where it is amplified and passed to frequency modulator 74. Baseline correction circuit 75 maintains a proper baseline for the ECG signal. When the carrier wave is removed. Level detection circuit 34 reduces the time constant of baseline correction circuit 75. Consequently, each time that the respiration channel baseline is restored, the baseline for the ECG channel is also restored.

Returning to the respiration channel, it will be seen that the noise-free demodulated signal is amplified in amplifier 44 which passes the amplified signal to log amp 48. The baseline of the signal in amplifier 44 is corrected by baseline correction circuit 58 and an excessive deviation of the baseline is sensed by baseline detection circuit 54. Two baseline detection circuits are used so that baseline drift in any portion of the circuit will be detected and immediately corrected. It can be seen that detection circuit 52 will respond to any baseline drift in the respiration channel of the patient unit. Detection circuit 54 responds to baseline drift in amplifier 44. If the drift in the patient unit is in an opposite direction to the drift in amplifier 44, baseline detection circuit 54 will not produce an output. Nevertheless, detection circuit 52 will produce an output thus correcting the baseline. If the drift is only caused by amplifier 44, detection circuit 52 will not produce an output but detection circuit 54 will, thus ensuring that the deviation is promptly corrected for.

Baseline correction circuit 58 normally operates in a very slow mode to follow the DC offset of the slow respiration data signal. However, when an excessive baseline deviation is to be compensated for, circuit 58 is operated in the fast mode by actuating circuit 63 through microprocessor 56. In the fast operational mode, circuit 58 will rapidly follow the DC offset of the respiration data signal. To avoid discontinuity in the baseline due to switched baseline time constants, a medium variable circuit 64 is actuated after fast correction circuit 63 is deactuated to allow baseline correction circuit 58 to follow the DC offset of the respiration data signal more accurately. The variable circuit can change the time constant to slow gradually over a period of several minutes following deactuation of circuit 58.

Returning again to the ECG channel, it will be seen that the noise-free demodulated ECG data signal is amplified at amplifier 80 and passed through switch 82 and AGC circuit 84 to signal shaping circuit 86. Baseline correction circuit 90 compensates for baseline drift of the ECG data signal. When the baseline drift becomes excessive, detector 88 signals microprocessor 56 to operate the baseline circuit in a fast mode through fast circuit 93. In the system of the present invention, baseline correction circuit 90 and baseline correction circuit 58 are both operated in the fast mode at the same time, and switches 45, 46 and 82 are opened at that time so that no output is transmitted to a display device while rapid baseline correction is being effected.

The ECG data signal passed through AGC circuit 84 is output to shaping circuit 86 and to output line 77 through switch 101 with an amplitude which is maintained within predetermined limits. The ECG data signal passed through amplifier 80 is output to line 100 through switch 82, but with an amplitude which is not controlled, representing 1 v output on line 100 for 1 mv input ECG signal. Shaping circuit 86 contains a filter which is designed to pass the R wave portion of the ECG signal. Microprocessor 56 senses the R wave portion of the ECG signal on line 87 and, if the signal is missing, causes a rapid increase in the gain of AGC circuit 84 through line 65 to ensure that the missing signal is not due to poor gain in the circuit. This feature is of much value in avoiding false bradycardia and cardiac arrest alarms after some artifact causes radical AGC gain reduction.

FIG. 1 also shows a power supply 95 for the circuits of the present invention. Power supply 95 will be discussed in detail hereafter. An apnea time delay switch 96 is also shown. Switch 96 can have two or more settings and provides signals to microprocessor 56 relating to a minimum time period for defining an apnea event. Finally, a reset switch 97 is shown. Switch 97 includes two contacts which send a ground signal, respectively, through line 98 to power supply 95 and through line 99 to microprocessor 56. As will be discussed in detail, in order to turn off power supply 95 or to change the position of apnea switch 96, reset switch 97 must be actuated, otherwise an alarm signal is produced. This feature prevents tampering with the switch settings of the present invention.

Figure 2:
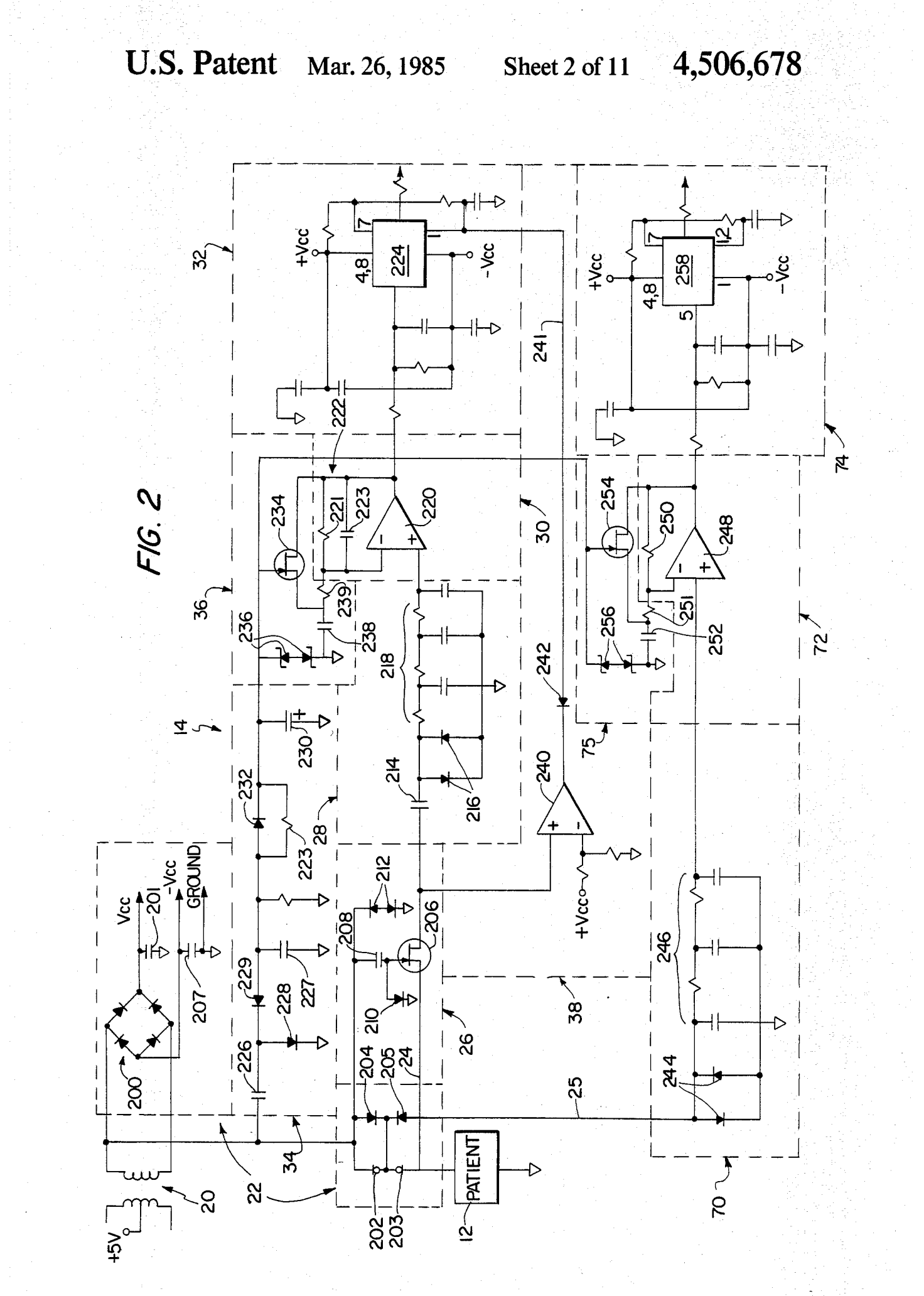

FIG. 2 shows the patient unit 14 of the present invention connected to isolation transformer 20. The primary of isolation transformer 20 is connected to a 100 khz voltage source so that the secondary of the transformer delivers a 100 khz signal to input circuit 22 which includes rectifier bridge 200 that produces a full wave rectified DC output that is used for the bias voltages of the patient unit. The DC output signal of rectifier bridge 200 is filtered by capacitors 201 and 207. The input circuit also includes back-to-back constant current diodes 202 and 203 and steering diodes 204 and 205. Diode 204 passes the positive half waves of the carrier signal to constant current diode 203, and steering diode 205 passes the negative half waves of the carrier signal to constant current diode 202. The output of this diode network is connected to patient 12 through a carbon or silver chloride electrode, as is standard in the art. The patient is also connected to a floating ground.

As discussed above, the carrier signal is modulated in the patient's body in accordance with respirations so that an amplitude modulated respiration signal is produced. This signal is passed along line 24 to synchronous detector 26 which comprises FET 206, the gate of which is connected through diode 210 to the floating ground and through capacitor 208 to the carrier signal input. The input to capacitor 208 is also connected through back-to-back zener diodes 213. Diode 210 clamps the gate of FET 206 to the floating ground and zener diodes 212 act as input protection for the FET. Capacitor 208 AC couples the carrier signal to the FET gate so that FET 206 is turned on in response to peaks of the carrier signal thus providing synchronous detection for the amplitude modulated respiration signal. The detected respiration signal is passed to filter section 28 which AC couples the signal through capacitor 214 to filter 218. Clamping diodes 216 clamp the positive and negative going portions of the signal to the floating ground to protect the circuit from voltages due to, for example, defibrillation of the patient. Filter section 218 is a low pass filter which smooths the signal and passes it to amplifier 220. Amplifier 220 contains a feedback network 222 having resistor 221 and capacitor 223. Amplifier 220 provides a substantial gain increase to the signal and passes it to frequency modulator 32. Frequency modulator 32 is a voltage controlled oscillator (VCO) comprising an integrated circuit voltage controlled oscillator 224 which can be an Intersil ICM 7555 integrated circuit having an appropriate biasing network. Also, voltage controlled oscillator 24 has an enable input connected to line 241. Line 241 is connected through diode 242 to comparator 240. The non-inverting lead of comparator 240 is connected to the output of FET 206, and the inverting input connected to a positive voltage source. When a loose lead connection exists and the output of FET rises to a level indicative of 1500 ohms or greater, comparator 240 outputs a signal through diode 242 to disable VCO 224.

Baseline correction circuit 36 essentially comprises a capacitor 238 which senses the fed back output of amplifier 220 through resistors 221 and 239 and charges in accordance with the DC level thereof. The voltage developed on capacitor 238 is fed to the inverting input of amplifier 220 and, accordingly, the DC level at the inverting input of amplifier 220 equals the DC level of the non-inverting input of the amplifier so that the output has a baseline at zero volts. Baseline correction circuit 36 also includes FET 234 which shunts resistors 221 and 239. The gate of FET 234 is connected to level detection circuit 34. Level detection circuit 34 comprises a clamping circuit consisting of capacitors 226 and 227, and diodes 228 and 229. This clamping circuit receives a carrier signal and doubles the carrier voltage and clamps it below the floating ground. Capacitor 230 receives the output of the clamping circuit through resistor 233 and charges to an average DC level determined by the received signal. The charge on capacitor 230 holds the gate of FET 234 negative so that FET 234 is turned off when a carrier signal is present. When the carrier is interrupted, capacitor 230 rapidly discharges through diode 232 and the voltage on the gate of FET 234 is raised so that capacitor 238 is shunted to the output of amplifier 220. This action greatly reduces the charging time constant of capacitor 238 which tne quickly restores the baseline to its proper level.

In operation, bias voltages are produced from the carrier signal and applied to the active components of the respiration channel of the patient unit. Also, the carrier signal is dropped in voltage through steering diodes 204 and 205 to a level below 0.5 volts, and the current of the carrier signal is controlled to be approximately 600 ua by constant current diodes 202 and 203. The modulated respiration signal from patient 12 is detected by FET 206 and AC coupled by capacitor 214 to filter section 218 where the signal is smoothed. The filtered signal is amplified by operational amplifier 220, the output of which is sensed by capacitor 238 which maintains a voltage at the inverting input of amplifier 220 which is equal to the DC offset of the signal at the non-inverting amplifier input. The output of amplifier 220 is frequency modulated by voltage controlled oscillator 214 unless a patient lead is loose, in which case operational amplifier 240 disables the voltage controlled amplifier.

If the DC offset of the ECG data signal becomes too great, microprocessor 56 shuts off the carrier signal. The time during which the carrier signal is removed is not sufficient for capacitors 201 and 207 to discharge, the bias voltages are not removed from the active elements of the circuit. The capacitor 230 discharges thus turning on FET 234 thereby reducing the charging time constant of capacitor 238. After a predetermined time, the carrier is turned back on and circuit operation is resumed.

The ECG channel receives a signal on line 25 which is input to filter section 70. Clamping diodes 244 clamp the signal within predetermined limits of the floating ground and filter section 246 passes only the ECG signal and filters out the 100 Khz respiration signal and spurious signals due to, for example, defibrillation of the patient or the like. The filtered ECG signal is received by amplifier 72 which comprises operational amplifier 248 and feedback resistor 250. Any DC offset in the ECG signal is compensated for by capacitor 252 which also receives the output of operational amplifier 248 through resistors 250 and 251. Finally, the output of operational amplifier 248 is passed to frequency modulation circuit 74 which comprises integrated circuit voltage controlled oscillator 258 which can be an Intersil ICM 7555 integrated circuit which is appropriately biased.

Capacitor 252 can be connected directly to the output of operational amplifier 248 by FET 254. The gate of FET 254 is protected by back-to-back zener diodes 256 and is also connected to the output of level detection circuit 34.

In operation, the ECG signals are clamped by diodes 244 and filtered by filter section 246. The filtered ECG signals are amplified in operational amplifier 248 and the DC offset of the signal is reduced to zero by a charge on capacitor 252. When the offset on either the respiration channel or the ECG channel becomes too great, microprocessor 56 causes FETs 234 and 254 to turn on thus reducing the charging time constants of capacitors 238 and 252.

Figure 3:
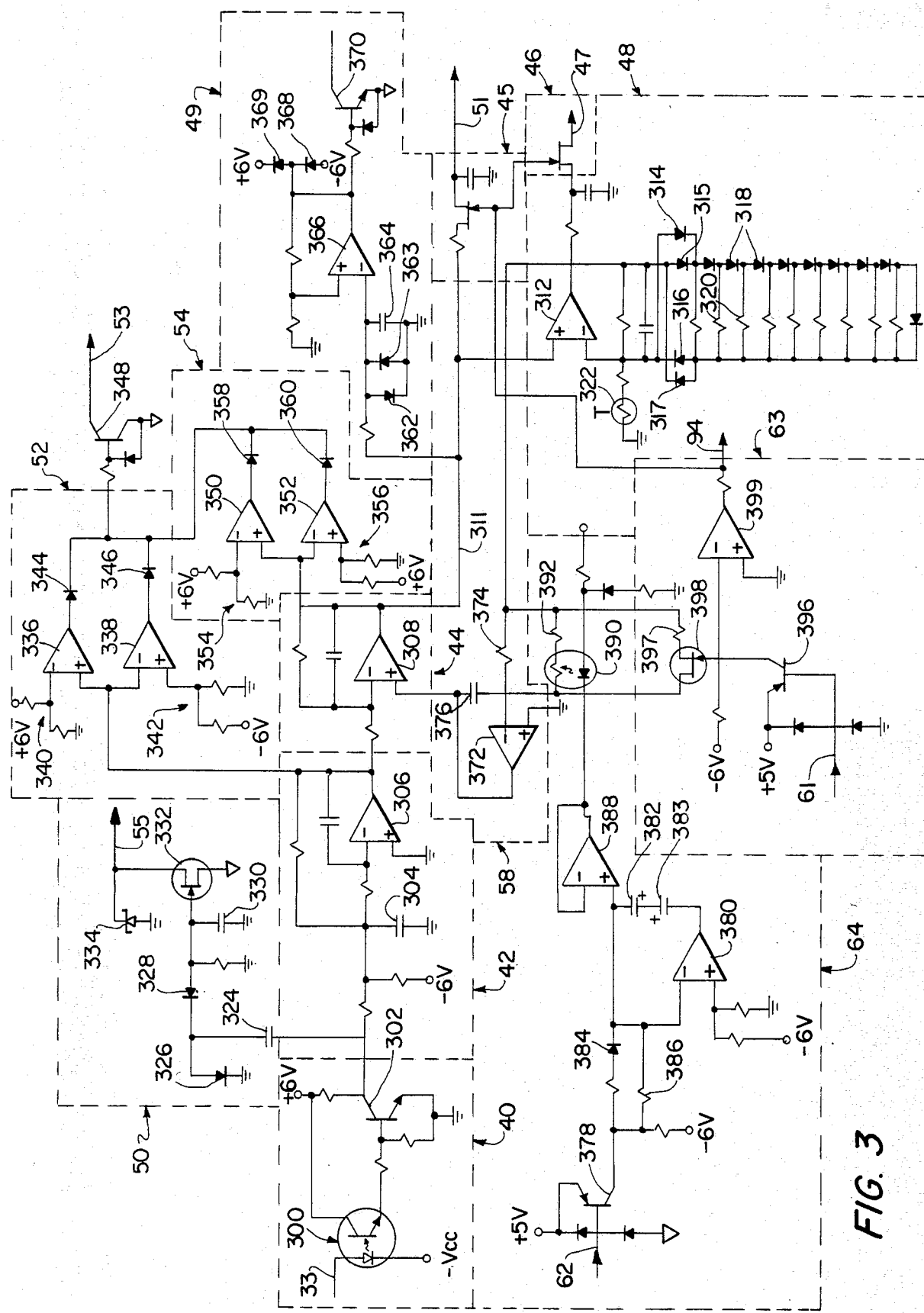
FIG. 3 is a schematic diagram showing the respiration channel of the signal analysis unit of the present invention.

FIG. 3 shows the respiration channel of the signal analysis unit of the present invention. The respiration channel is isolated from the patient unit by optical coupler 300 which receives the frequency modulated respiration signal on line 33 and optically couples this signal to transistor 302. The isolated signal from transistor 302 is passed to demodulation circuit 42 which comprises a low pass filter which includes capacitor 304, and an integrator which receives the output of the low pass filter. The integrator is formed from operational amplifier 306 and a feedback capacitor. The demodulated signal is connected to the inverting input of amplifier 308 which is biased to provide gain to the signal and pass only the frequencies of interest. A linear output from amplifier 308 is provided on line 311 to switch 45 which comprises a single FET having an output connected to line 51. The output of amplifier 308 is also provided to logarithmic conversion circuit 48. Circuit 48 includes operational amplifier 312, the output of which is fed back to its inverting input through steering diodes 314–317 and a ladder network comprising diodes 318 and resistors 320. Diodes 318 are connected in series and each has its anode connected to one terminal of a resistor 320. The opposite terminals of resistors 320 are connected together and to the anodes of diodes 316 and 317. Temperature compensation is provided by thermistor 322. As can be seen, the output of operational amplifier 312 is fed back through the appropriate steering diodes and one or more of diodes 318 to the inverting input of the amplifier. Accordingly, the output of amplifier 312 is the logarithm of the input. As the input voltage increases, diodes 318 are incrementally included in the feedback path to increase the range of the logarithmic amplifier. The log output is provided on line 51 through switch 46, which comprises a single FET, to output line 47.

Also connected to the output of transistor 302 is the loose lead detector 50 which comprises input capacitor 324, clamping diode 326 and steering diode 328. Steering diode 328 is connected to the gate of FET 332. A capacitor 330 is also connected to that gate. The output of FET 332 is presented to the microprocessor through line 55. A zener diode 334 provides input protection for the microprocessor. Clearly, when no signal is present on line 33, the voltage to the gate of FET 332 increases and a low signal is passed along line 55 to the microprocessor.

The output of operational amplifier 306 is also passed to baseline detection circuit 52 which comprises comparators 336 and 338. The inverting input of comparator 336 is connected to a positive voltage source and the non-inverting input of comparator 338 is connected to a negative voltage source. The output of comparator 306 is connected to the non-inverting input of comparator 336 and the inverting input of comparator 338. Accordingly, if the level of the signal from comparator 306 goes above or below the level indicated by positive voltage source 340 or negative voltage source 342, respectively, a signal will be passed through diode 344 or 346, respectively, to transistor 348 to turn that transistor on and pass a signal through line 53 to the microprocessor.

Similarly, a second baseline detection circuit 54 is connected to the output of operational amplifier 308. Baseline detector 54 is identical to offset baseline detector 52 and comprises comparators 350 and 352, voltage sources 354 and 356, and diodes 358 and 360. The output of circuit 54 sends a signal to the microprocessor through transistor 348.

The output of operational amplifier 308 is also passed to signal shaping circuit 49 which comprises clamping diodes 362 and 363, capacitor 364, operational amplifier 366 and output transistor 370. The signal to shaping circuit 49 is clamped by diodes 362 and 363, averaged by capacitor 364 and fed to amplifier 366. Amplifier 366 is connected with positive feedback to produce a square wave with hysteresis each time that the respiration data signal goes above and below zero. The output of amplifier 366 is clamped to ±6 volts by diodes 369 and 368, respectively. The output is also connected to the input of transistor 380 which passes the shaped signal to the microprocessor.

The output of logarithmic amplifier 48 is fed back to the input of baseline correction circuit 58. Circuit 58 comprises resistor 374 and an integrator comprising operational amplifier 372 and capacitor 376. The output of operational amplifier 372 is connected to the non-inverting input of amplifier 308. Accordingly, it can be seen that as the average signal from logarithmic amplifier 48 deviates from zero volts, the output of amplifier 372 will fluctuate and be added to the respiration data signal in amplifier 308 to return the baseline to zero volts.

The charge on capacitor 376 can be varied more rapidly by turning on FET 398 of the fast correction circuit 63. FET 398 is effective to place a low value resistance 397 in parallel with resistor 374. Accordingly, by turning on FET 398, the charge on the integrator of the baseline correction circuit 58 will be allowed to vary more rapidly. The gate of FET 398 is connected to the output of transistor 396, the base of which is connected through line 61 to an output of the microprocessor. Accordingly, the microprocessor can turn on FET 398 by an appropriate signal on line 61. The output of transistor 396 is also passed to operational amplifier 399 which sends an output to turn off switches 45 and 46 by applying a negative signal to their gate inputs, and thus eliminate the linear respiration output on line 51 and the logarithmic output on line 47. Consequently, a display of the respiration signal will be stopped during the fast restore period.

Due to the extremely slow frequency of the respiration data signal, it may be useful to restore the baseline to the appropriate level by varying the charge on the integrator of baseline correction circuit 58 at a rate which is intermediate that provided by resistors 374 and 397. Accordingly, a medium slow charge circuit is included which comprises variable resistor optical coupler 390 which has a variable resistance in series with resistor 392. This series resistance is in parallel with resistor 374. Accordingly, when optical coupler 390 is turned on, a medium resistance is placed in parallel with high value resistance 374. Optical coupler 390 has a control input connected to the output of buffer 388. The intput to buffer 388 is received from line 62 through transistor 378 and diode 384. Transistor 378 is also connected through resistor 386 to the input of an integrator comprising operational amplifier 380 and capacitors 382 and 383. Clearly, the rate of charge can be varied by the microprocessor when a signal is provided on line 62 to turn on transistor 378. The signal immediately causes a variation in the resistance of optical coupler 390, thus varying the time constant of the baseline correction circuit. Also, this time constant is reduced in accordance with the amount of time the signal is maintained by the integrator comprising amplifier 380 and capacitors 382 and 383. Back-to-back polar capacitors are used in the integrator to allow the integrator to output either polarity. The integrator charging time is rapid, so that the variable time constant rapidly changes toward fast under microprocessor control. Integrator discharge time is slow so that the variable time constant slowly changes toward slow under the microprocessor control.

In operation, when a signal is received by optical coupler 300, that signal is electrically isolated from the patient unit and passed to the demodulation circuit which includes capacitor 300 and integrator 306. If no signal is received, the microprocessor is notified through FET 332 and line 55, and a loose lead alarm is actuated.

The offset level of the demodulated output is compared in comparators 336 and 338 to maximum and minimum permissible levels and, if the baseline is not within the prescribed range, transistor 348 is actuated to notify the microprocessor.

The demodulated respiration data signal is amplified in amplifier 308. The offset of the amplifier output is again checked with permitted maximum and minimum values and, if outside the acceptable range, the microprocessor is notified by a signal from transistor 348. The ECG data signal is also directly passed to positive feedback amplifier 366 which acts as a zero crossing detector to notify the microprocessor of each respiration event through transistor 370. Further, the amplified ECG data signal is passed to switch 45 which, if fast restoration of the baseline is not being performed, passes the signal to linear respiration output lead 51. The linear output is also passed to logarithmic amplifier 48 which logarithmically amplifies the signal and passes it through switch 46 to output line 47. If a display of the signal is required, an appropriate display device can be attached to either line 47 or line 51.

If fast baseline restoration is required, a signal is produced on line 61 which turns on FET 398 to place resistor 397 in parallel with resistor 374 thus reducing the time constant of the baseline correction circuit. After fast baseline restoration is complete, medium slow variable baseline restoration is effected by a signal on line 62 which controls the resistance of optical coupler 390 which is placed in series with resistor 392 and which combination is placed in parallel with resistor 374. The medium slow variable baseline rate is controlled by the output of the integrator circuit comprising operational amplifier 380 and capacitors 382 and 383.

Figure 4:
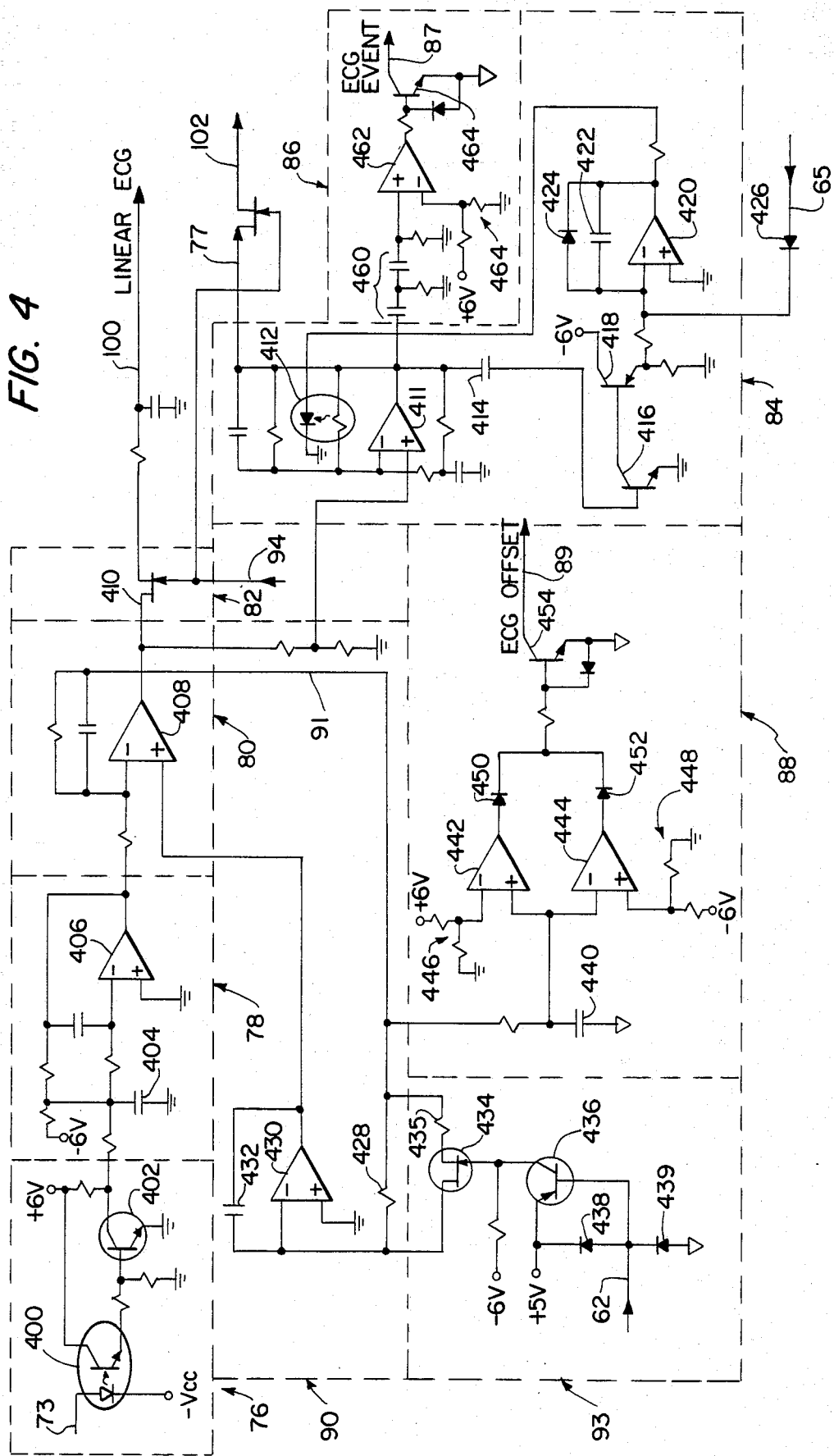
FIG. 4 is a schematic diagram showing the ECG channel of the signal analysis unit of the present invention.

FIG. 4 shows the ECG channel of the signal analysis unit. An isolation device 76 comprising optical coupler 400 receives frequency modulated ECG signals on input line 73 and passes an output through transistor 402 to the ECG channel. The ECG channel includes a frequency demodulator comprising a low pass filter which includes capacitor 404, and an integrator comprising operational amplifier 406 with a capacitor in its feedback loop. The demodulated signal is passed to an amplifier comprising operational amplifier 408 having a feedback network connected to its inverting input so that the amplifier will pass only frequencies associated with the ECG signal. The output of operational amplifier 408 is passed to switch 82 comprising a single FET 410 which, when on, passes the signal to output line 100. The output of amplifier 408 is also passed to automatic gain control circuit 84. Automatic gain control circuit 84 includes operational amplifier 411 which is biased as a linear amplifier and also includes the variable resistance portion of a variable resistance optical coupler 412 in its feedback loop. The output of operational amplifier 411 is AC coupled through capacitor 414 to the input of transistor 418. The input of transistor 418 is clamped to ground by diode 416. Transistor 418 feeds an integrator comprising operational amplifier 420 and capacitor 422. The charge on capacitor 422 is clamped in a forward direction by diode 424. Capacitor 414 and diode 416 act to clamp the signal input to transistor 14 to ground. Accordingly, the integrator reacts to the peak amplitude of the ECG signal and, when the amplitude increases, the output of integrator 420, 422 also increases thus decreasing the resistance of optical coupler 412 and thereby decreasing the gain of amplifier 411.

The output of amplifier 411 has a constant peak amplitude and is passed through switch 101 to output line 102 and to signal shaping circuit 86. Circuit 86 comprises a filter portion 460 which passes the R wave portion of the ECG data signal. The R wave portion is received by the non-inverting input of operational amplifier 462 and compared with a voltage source 464. If the R wave is greater than the voltage set by source 464, a square wave output is passed through transistor 464 to line 87 and to the micro-processor. A linear ECG signal is made available at the output of FET 410 on line 100, and a gain controlled signal is made available on line 102.

The output of operational amplifier 408 is fed back through line 91 to baseline correction circuit 90. Baseline correction circuit 90 comprises a high value resistance 428 which feeds the input of an integrator comprising operational amplifier 430 and capacitor 432. The output of integrator 430, 432 is fed to the non-inverting input of operational amplifier 408. Accordingly, as the DC offset of the output of amplifier 408 changes, the charge on integrator 430, 432 changes also and nullifies the DC offset. Fast baseline correction circuit 93 comprises FET 434 which, when turned on, connects low value resistance 435 in parallel with resistance 428. FET 434 is turned on by transistor 436 in response to a signal from the microprocessor on line 62. Line 62 is clamped by diodes 438 and 439. Line 91 is also connected to an offset detection circuit 88 which comprises comparators 442 and 444 which have their non-inverting and inverting inputs connected respectively to line 91. Capacitor 440 is connected to line 91 also for averaging the signal applied to comparators 442 and 444. Comparator 442 compares the signal on line 91 to a positive voltage provided by source 446, and comparator 444 compares the signal on line 91 to a negative voltage provided by voltage source 448. Comparators 442 and 444 provide outputs if the offset of the signal on line 91 is above or below the voltages set by sources 446 and 448, respectively. These outputs are passed through diodes 450 and 452, respectively, to transistor 454 which sends a signal through line 89 to the microprocessor.

In operation, optical coupler 400 feeds transistor 402 which provides an isolated frequency modulated ECG signal to demodulator 78. The signal is low pass filtered and integrated in the demodulator and passed to operational amplifier 408 in which the signal is amplified. Any offset in the signal is fed back through line 91 to charge integrator 430, 432 which then reduces the offset at amplifier 408. If fast baseline correction is required, a signal is provided at line 62 which turns on FET 434 and reduces the time constant of the integrator. At the same time, a signal is provided on line 94 to switch off switches 82 and 101. The signal on line 91 is also sensed by amplifiers 442 and 444 which feed a signal through line 89 if a DC offset is too great. In response to such a signal, the microprocessor may begin fast offset correction.

When FET 410 of switch 82 is turned on, the baseline corrected signal is passed to line 480 which may be connected to a display device or the like. The signal is also passed to the automatic gain control circuit. Initially, the signal is received by amplifier 411 which is controlled to have a maximum gain. This high gain signal is passed through transistor 418 to integrator 420, 422 which reduces the gain of amplifier 411 to the desired amount. The output of integrator 420, 422 then controls the gain of amplifier 411 so that the peak amplitude of the ECG signal is maintained at a desired level. The gain controlled signal is filtered at filter 460 and squared in differential circuit 462 and passed through line 87 to the microprocessor. If the signal at the microprocessor disappears, a signal can be passed through line 65 and diode 426 to rapidly decrease the output of integrator 420, 422 thus increasing the gain of amplifier 411 to its maximum in an attempt to restore the signal level.

Figure 5:
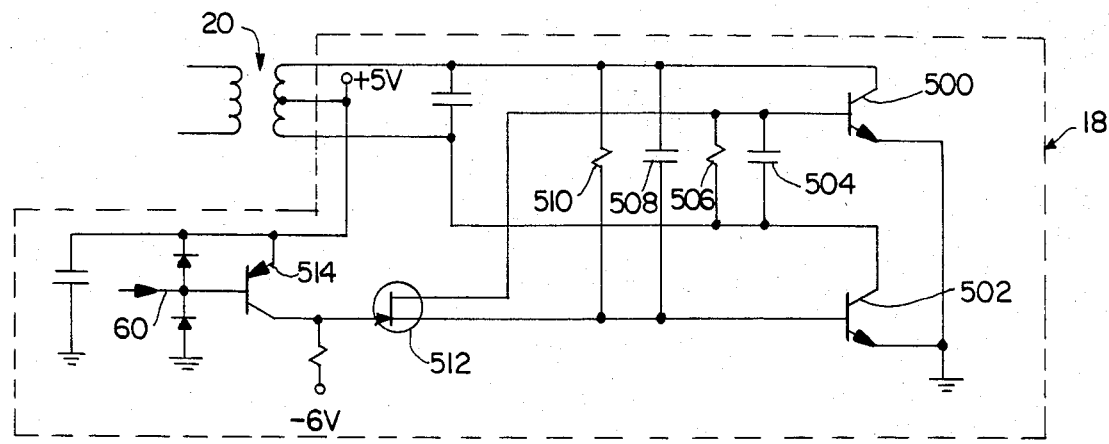
FIG. 5 is a schematic diagram of the carrier signal generation unit of the present invention.

FIG. 5 shows the carrier generator 18 of the present invention. Generator 18 comprises an astable multivibrator formed from transistors 500, 502, capacitors 504, 508, and resistors 506, 510. The collectors of transistors 500, 502 are fed from a 5 volt supply through opposite halves of the center tap primary of transformer 20. The astable multivibrator operates in a conventional manner. When the carrier signal is to be removed, the microprocessor sends a ground signal through line 60 to transistor 514. Transistor 514 is turned on, thus turning on FET 512. FET 512 shorts out the bases of transistors 500, 502 to stop the operation of the multivibrator.

FIGS. 6a, 6b, 7a, 7b and 7c show flow charts for the main and interrupt service programs used by microprocessor 56 in the present invention.

The interrupt service program is executed once every millisecond. This program is entered at step 700, at which time certain initialization functions are performed as would be obvious to one of ordinary skill in the art. At step 702, registers ECGNEW and RESNEW are incremented. At step 660, the setting of apnea switch 96 is stored in a register called SW. At step 662, the contents of SW are compared with the contents of a register called APNEA which stores the last valid setting of the apnea switch. If the apnea switch setting has been changed, step 664 passes control to step 666 which determines whether the mismatch FLAG has been set. If the mismatch FLAG has been set, control passes to step 668 which sets a tamper alarm. If the mismatch FLAG has not been set, control passes to step 670 which determines whether a ground signal is present on line 99 indicating that reset switch 97 has been actuated. If the reset switch is depressed, control passes to step 672 which stores the new apnea switch setting in APNEA. If the reset switch is not depressed, control passes to step 674 which sets the mismatch FLAG.

If, at step 664, the apnea switch has not been changed, control passes to step 676 which clears the mismatch FLAG. Control is then passed to step 678 which dtermines whether reset switch 97 is depressed. If switch 97 is depressed, control passes to step 680 which clears the tamper alarm.

As can be seen from the above description, this portion of the program causes an alarm to be set if the apnea switch setting has been changed without the reset switch being depressed and the changed setting is held for two cycles of the interrupt service routine. On the first cycle, the mismatch FLAG is set at step 674 and on the second cycle, the tamper alarm is set at step 668. However, if the reset switch is depressed when the apnea switch setting is changed, steps 670 and 672 cause the new setting to be stored as a valid apnea time. Once a tamper alarm has been set, in order to clear this alarm, the apnea switch 96 must be returned to its original, valid setting and reset switch 97 must be depressed. This action causes control to be passed from step 664 through steps 676 and 678 to step 680 which clears the tamper alarm.

After steps 668, 672, 674 or 680, control is passed to step 705. At step 704, a clock register is checked to determine whether an increment of 128 milliseconds has occurred. For each increment of 128 milliseconds, control passes to step 706, at which time lines 53 and 89 are checked to determine whether the respiration or ECG baseline signals are excessive. If the signals are off scale, a register named OFF is set to be equal to 255 in step 708. Thereafter, the contents of OFF are decremented by 1 in step 710. If the ECG or respiration signals are not off scale, OFF is also decremented by 1 in step 710. Accordingly, it will be seen that once OFF is set to 255, it takes approximately 32 seconds for the contents of that register to be decremented to zero, since step 706 is performed approximately once every eighth of a second. In step 712, the contents of OFF are checked. If the contents are greater than 253, control passes to step 714, which controls the carrier kill circuit. The carrier is killed through line 60. If the contents of OFF are less than 253, control passes to step 716, which restores the carrier. Control is then passed to step 718 where the contents of OFF are checked to see if they are greater than or equal to 240. If the contents of this register are greater than or equal to 240, step 720 sets the fast ECG baseline by passing a signal through line 61. Otherwise, the fast ECG baseline is cleared at step 722. Control is then passed to step 724 which checks to see if the contents of OFF are greater than or equal to 232. If greater, control is passed to step 726, which sets the fast respiration baseline by passing a signal through line 61. Otherwise, the fast respiration baseline is cleared at step 728. Control is then passed to step 730 where OFF register is checked to see if its contents are greater than zero. If greater, the medium respiration baseline is set at step 732 by passing a signal through line 62. Otherwise, the medium respiration baseline is cleared in step 734. Control passes from step 732 or 734 to step 736. Likewise, if a 128 millisecond increment has not been determined at step 704, control passes directly to step 736. At step 736, input line 87 is checked to determine if a square wave input is present, indicating a new ECG event. If an event has occurred, control passes to step 738 where the contents of the ECGNEW register pair is moved to the ECGOLD register pair, thus providing a determination of the increment between the last two ECG events in the ECGOLD register pair. The ECG event flag is set and the ECGNEW register pair is cleared. If no new ECG event has occurred or after the completion of step 738, control passes to step 740. Step 740 checks line 57 to determine whether a new respiration event has occurred in the form of a square wave signal on line 57. If a new respiration event has occurred, control passes to step 742 where the contents of the RESNEW register pair is moved to the RESOLD register pair, thus providing an indication of the interval between the last two respirations. The RES event flag is set and the RESNEW register pair is cleared. After completion of step 742, or if no new respiration event has occurred, control returns to the main program.

Figure 6A:
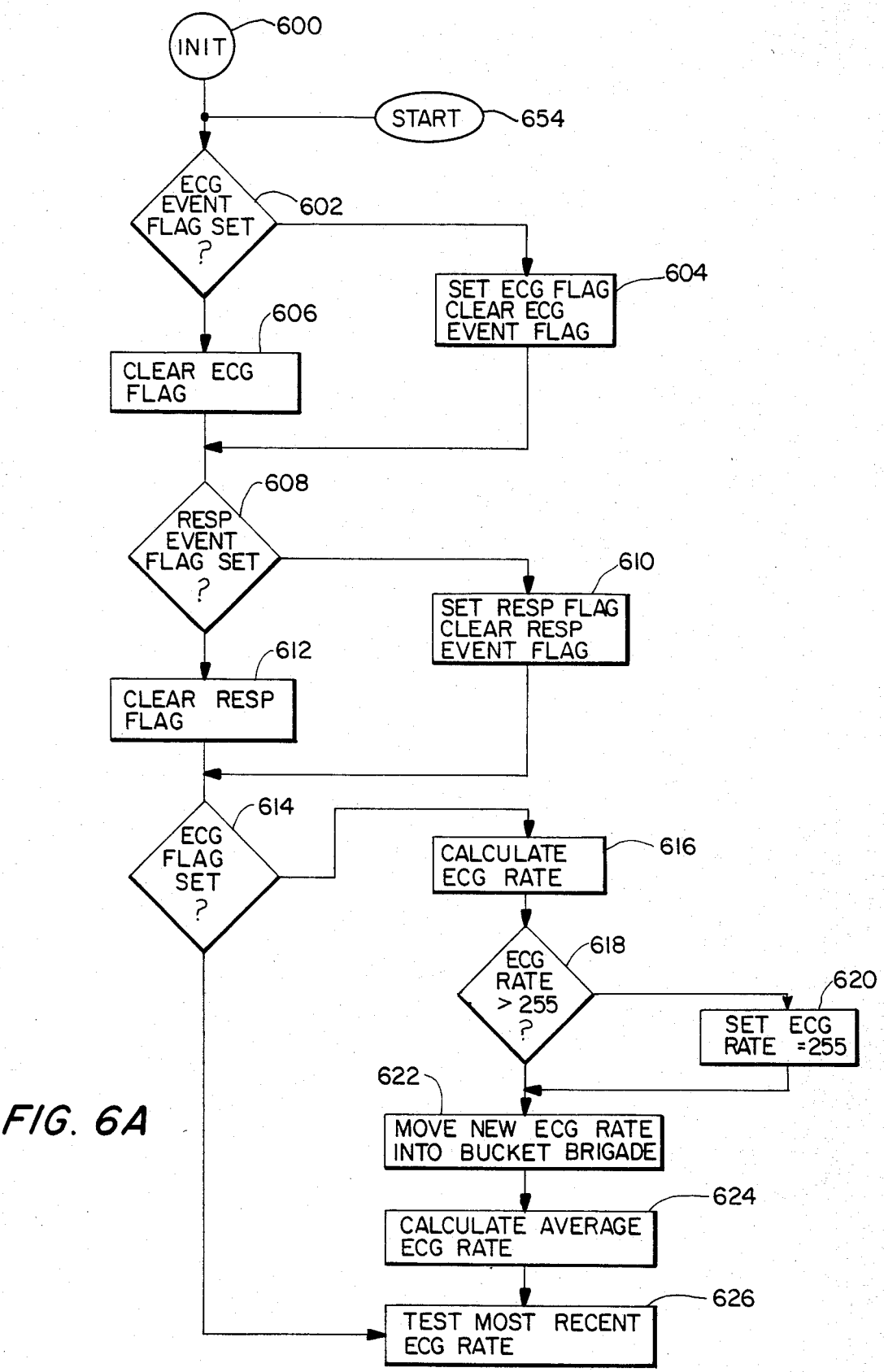
FIGS. 6a and 6b show a flow diagram of the main program used in the microcomputer of the present invention.
Figure 6B:
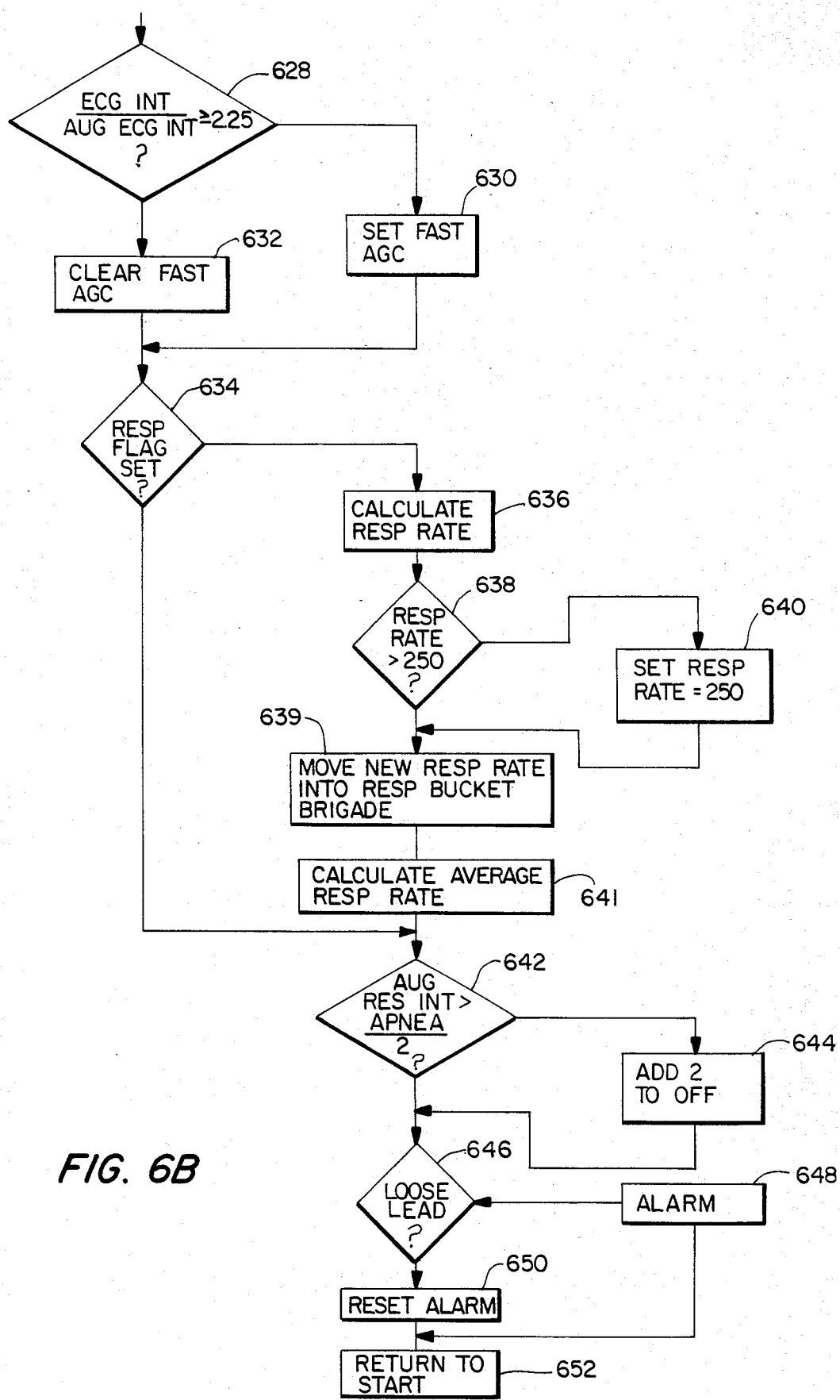

FIGS. 6a and 6b set forth the main program. The main program is initialized in step 600 and control is then passed to step 602 where the ECG event flag is checked. If the ECG event flag is set, control passes to step 604 where the ECG flag is set and the ECG event flag is reset. If the ECG event flag is not set, control passes to step 606 where the ECG flag is cleared. Control is then passed to step 608 where the respiration event flag is checked. If the respiration event flag is set, control passes to step 610 where the respiration flag is set and the respiration event flag is reset. If the respiration event flag is not set at step 608, control is passed to step 612 where the respiration flag is cleared. Control is then passed to step 614 where the ECG flag is checked. If the ECG flag is set, control passes to step 616 which calculates the ECG rate by dividing the contents of the ECGOLD register pair by 60,000 to provide a beats-per-minute indication. Step 618 determines whether the beats per minute is greater than 255. If the beats per minute is less than 255, the ECG rate register is provided with the actual ECG rate. Otherwise, the ECG rate register is set at 255 in step 620. In step 622, the new ECG rate is moved into a bucket brigade which stores the last 8 ECG rates. At step 624, the average ECG rate is determined by averaging the contents of the 8 buckets of the bucket brigade. At step 626, the most recent ECG rate is tested. This is accomplished by dividing the most recent ECG rate by a constant to provide an interval number and dividing the average ECG rate by a constant to provide an interval number. In step 628, the recent ECG interval is divided by the average ECG interval. The result is compared with 2.25. Returning for a moment to step 614, if the ECG flag is not set, the test in step 626 is performed on the previous most recent and average ECG rates. In step 628, if the recent ECG interval is equal to or greater than 2.25 times the average ECG interval, control passes to step 630, where the fast AGC is set by passing a signal on line 65. Otherwise, the fast AGC is cleared at step 632. Control is then passed to step 634 which checks to see if the respiration flag has been set. If the respiration flag has been set, control passes to step 636, which calculates the respiration rate by dividing the respiration interval in the RESOLD register pair by 60,000. If it is determined in step 638 that the respiration rate is greater than 250, the respiration rate register is set at 250 in step 640. Otherwise, the actual respiration rate is set in the respiration rate register. Control is then passed to step 639 where the new respiration rate is added to a bucket brigade. In step 641, the respiration average rate is determined. Control is then passed to step 642 where the average respiration interval is compared to the contents of APNEA divided by 2. As will be recalled, APNEA contains the last valid setting of APNEA switch 96. This will be a value of approximately 5 or 7 seconds. Of course, the values determined by APNEA switch 96 can be set at any amount desired. If the respiration flag has not been set at step 634, control passes directly to step 642. If it is determined that the average respiration interval at step 642 is greater than APNEA divided by 2, control passes to step 644, where OFF is incremented by 2. Control then passes to step 646, where the loose lead input is checked on line 55. If a loose lead condition is present, control is passed to step 648, which sets an alarm register. Otherwise, control is passed to step 650, which resets the alarm register. Control is then passed to step 652, which returns control to the start block 654, which then passes control to step 602 again.

Figure 7A:
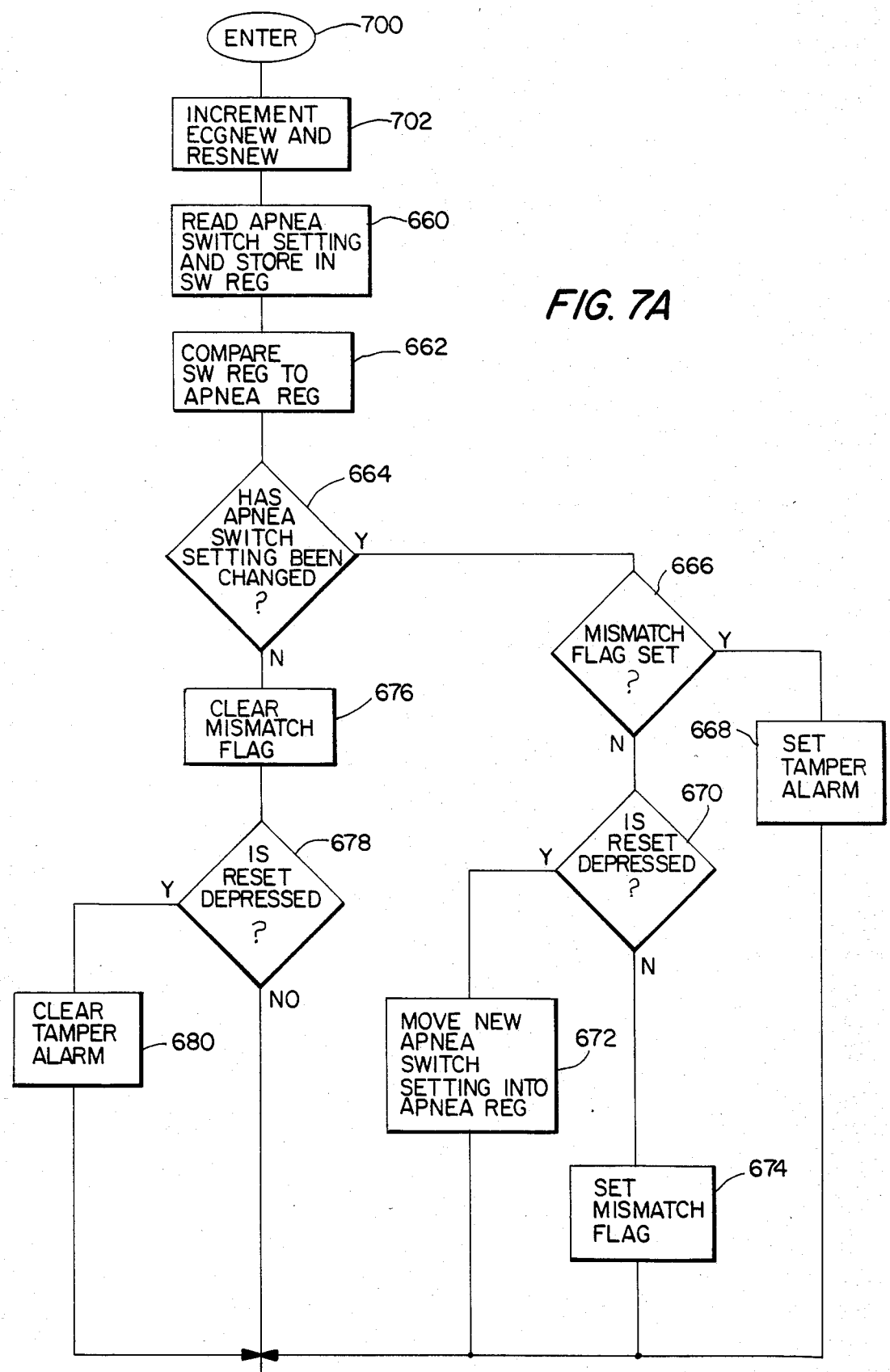
FIGS. 7a, 7b and 7c show a flow diagram of the interrupt service routine used in the microcomputer of the present invention.
Figure 7B:
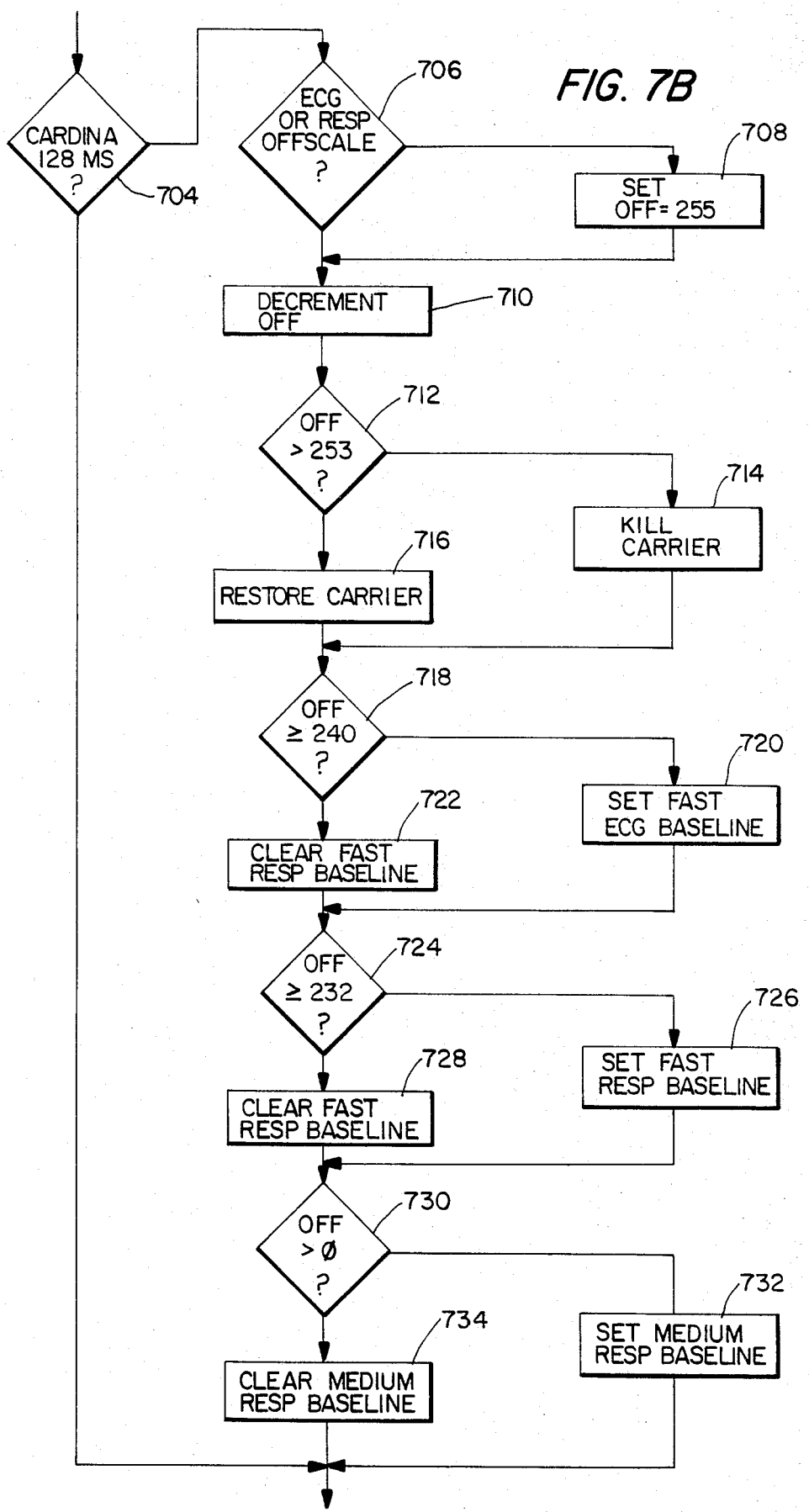
Figure 7C:
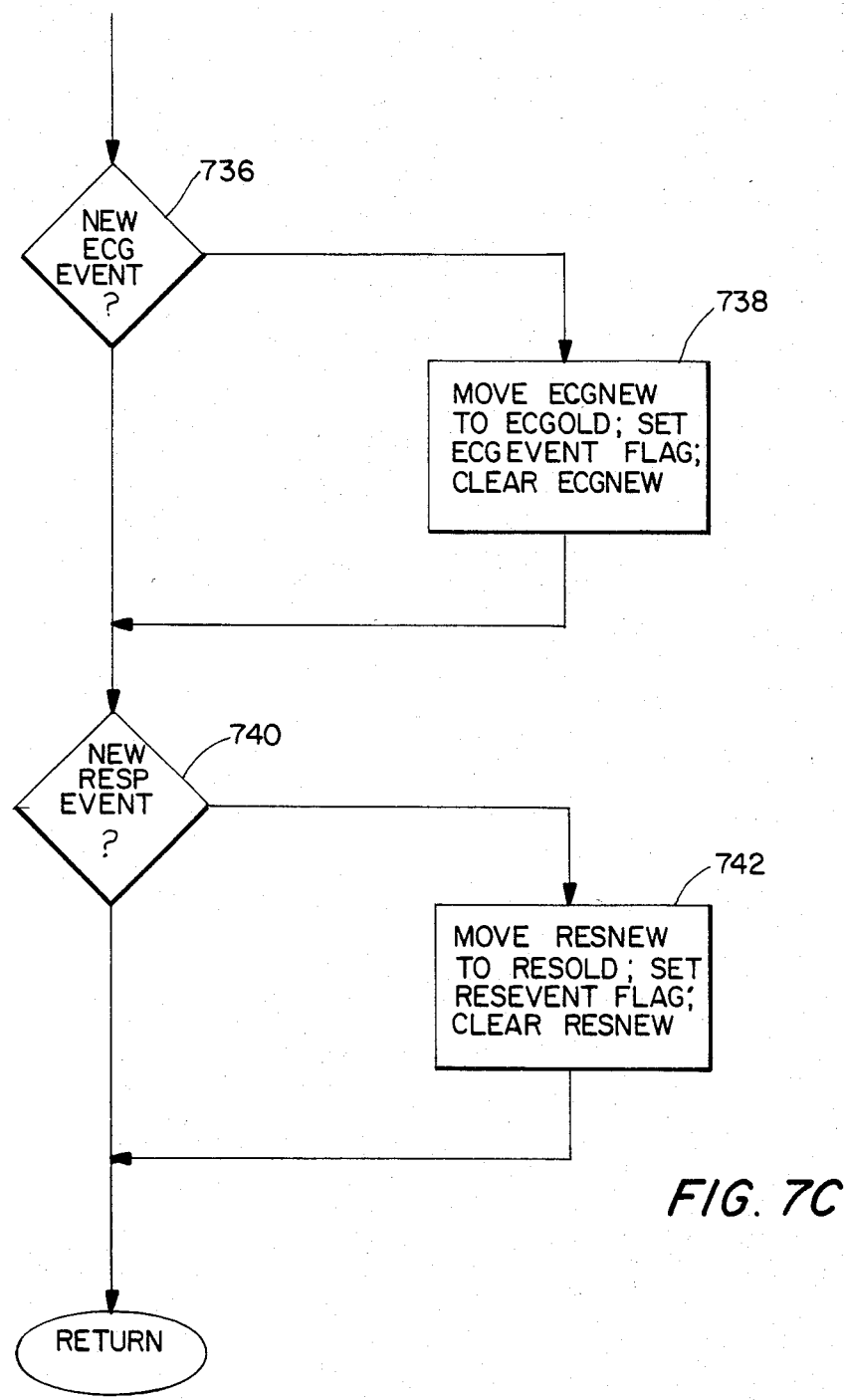

As will be understood from the foregoing explanation, every millisecond, the interrupt service routine of FIGS. 7a, 7b and 7c tests for a new ECG event and a new respiration event in step 736, and 740, respectively. When a new ECG event occurs, a number is stored in the ECGOLD register pair indicating the time interval in milliseconds between the last two ECG events. In like manner, a number is stored in the RESOLD register pair each time a new respiration event occurs. This number indicates in milliseconds the time interval between the last two respiration events. Upon each multiple of 128 milliseconds, input lines 53 and 89 are checked to determine if an off scale indication from baseline detection circuits 52, 54 or 88 is present. If an off scale indication is present, the carrier generator 18 is turned off through line 60 for a minimum of approximately one-eighth of a second at step 712 and 714. During this time, rapid baseline restoration is effected by circuits 36 and 75 in the patient unit. Also, steps 718 and 720 cause the fast baseline circuit 93 to be operative for approximately 2 seconds, during which time rapid baseline correction of the ECG data signal is performed by circuit 90. Also at the same time, steps 724 and 726 cause a rapid restoration of the respiration baseline through circuit 63 for approximately 3 seconds. Finally, medium-slow circuit 64 is set for approximately 32 seconds so that, after the rapid baseline correction of the respiration data signal is completed, medium-slow baseline correction continues for approximately another 30 seconds. The program then tests for new ECG and new respiration events as discussed above. Control then returns to the main program of FIGS. 6a and 6b.

As can be seen from the discussion above, the main program is operative to first determine if a new ECG event or new respiration event has been sensed by the interrupt program. If no new event has occurred, the program, at steps 626 and 628, tests to determine whether the last ECG interval is greater than the average interval by a predetermined amount. If the interval is greater, the faast AGC input line 65 would have been activated to increase the gain of AGC circuit 84 at step 630. If no new ECG event has occurred, the fast AGC input is held activated. The program then tests at step 642 to determine whether the previous respiration interval is greater than a normal respiration. If the last interval was greater, the medium-slow baseline respiration circuit 64 would have been activated by incrementing the OFF register by 2. Accordingly, if no new respiration event has occurred, the OFF register is again incremented by 2. The program then checks to determine whether a loose lead has occurred. If so, the alarm is sounded. If not, the program returns to step 654.

If an ECG event has occurred, the program calculates a new ECG average for the last 8 occurrences in step 624 and tests the most recent ECG against the average in steps 626 and 628. Again, if the most recent ECG interval is greater than the average by a predetermined amount, the fast AGC circuit is activated at step 630.

In like manner, if a new respiration event has occurred, a new respiration average is determined at step 639 and the average respiration interval is tested at step 642. If the interval is greater than set by APNEA switch 96 divided by 2, the OFF register is incremented by 2 so that the medium-slow respiration baseline correction circuit 64 is activated.

Figure 8:
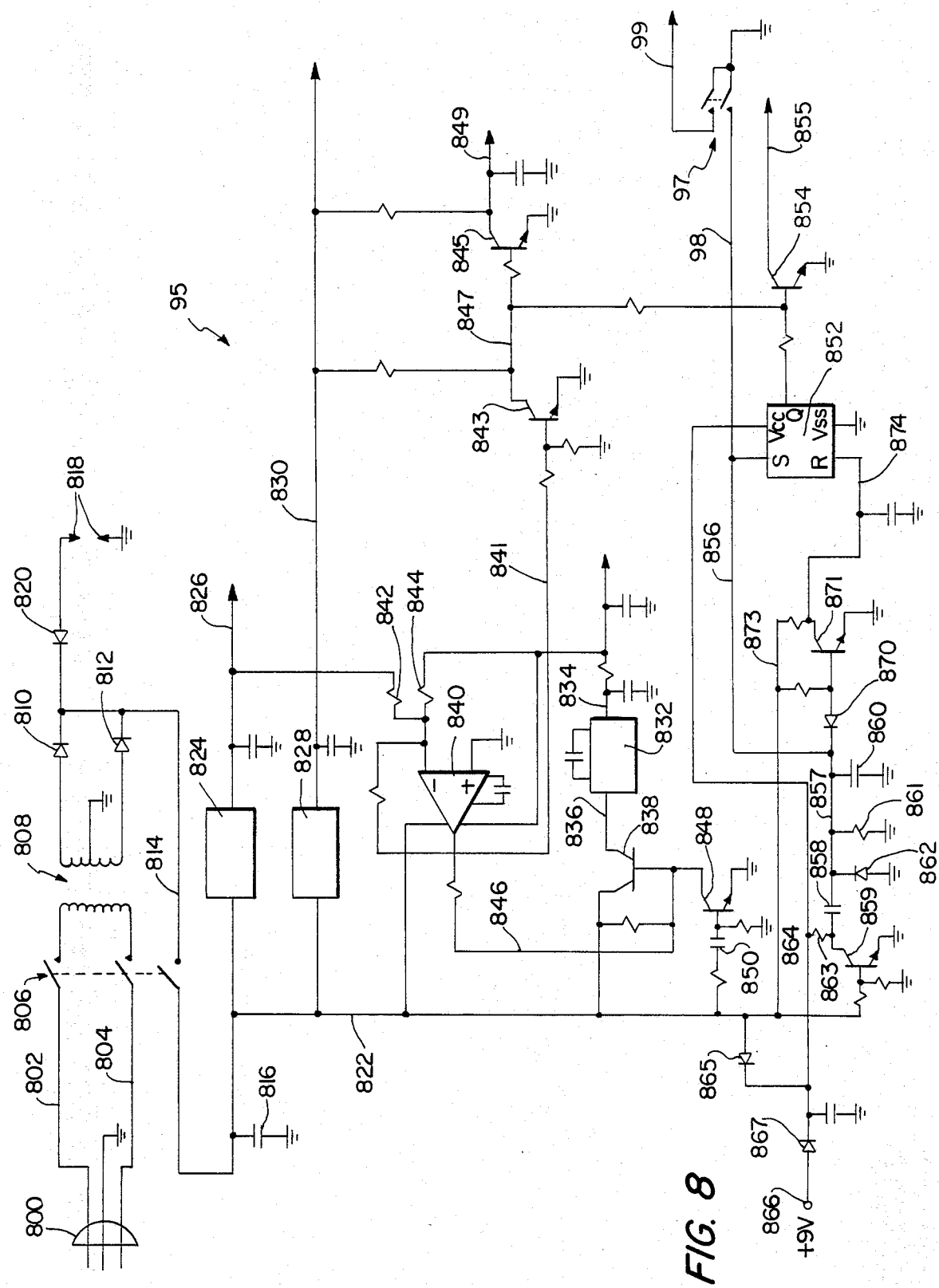
FIG. 8 is a schematic diagram of a power supply unit for use with the present invention.

FIG. 8 shows a power supply to be used with the present invention. The power supply 95 includes a standard three-pronged plug 800 which can be connected to a wall socket. Lines 802 and 804 receive current from plug 800 and pass the current through two poles of a three-pole switch 806 and a transformer 808. The current is rectified in diodes 810 and 812. The rectified current is passed through line 814 and the third contact of switch 806. The rectified current is filtered at capacitor 816. Alternatively, an external battery can be connected to the power supply through terminals 818 and diode 820. The filtered current from capacitor 816 is passed to unregulated supply line 822. A first integrated circuit voltage regulator 824 provides regulated positive 5 volts on line 826 for use in the analog circuits of the invention. A second integrated circuit voltage regulator 828 provides regulated +5 volts on line 830 for the digital circuits of the present invention. A negative 5 volt supply is provided by voltage mirror circuit 832 which produces an output on line 834 which is the negative of an input received on line 836. The input on line 836 is controlled by transistor 838 which receives an input from line 822. The conduction of transistor 838 is controlled by operational amplifier 840 which is biased to provide a gain of approximately 100. The non-inverting input of amplifier 840 is connected to ground. The inverting input of that amplifier has one lead connected through register 842 to the positive 5 volt supply on line 826. A second lead is connected through resistor 844 to the negative output of voltage mirror circuit 832. Accordingly, the voltage at the inverting input of amplifier 840 is the sum of the voltages on lines 826 and 834. The output of amplifier 840 changes in accordance with the sum of the voltages on lines 826 and 834, and is connected through line 846 to the base of transistor 838. Consequently, the conduction of transistor 838 is increased or decreased in accordance with the output of circuit 832 compared with the voltage on line 826. Accordingly, the negative 5 volt source is regulated in this manner.

A start-up transistor 848 has its collector connected to the base of transistor 838. Transistor 848 is momentarily turned on by capacitor 850 when switch 806 is closed. This initially turns on transistor 838 to ensure that an initial minus voltage is provided without delay.

The output of amplifier 840 is also passed through line 841 to the base of transistor 843. If the output of circuit 832 is correct, the output of amplifier 840 is slightly positive thus turning on transistor 843 through line 841. The collector of transistor 843 is connected to the base of transistor 845 through line 847. The collector of transistor 845 is connected to line 849 which actuates an alarm (not shown) when line 849 goes low. Clearly, when transistor 843 conducts, line 847 goes low and transistor 845 is non-conducting thus holding line 849 high. In the event that either too much current is drawn from circuit 832 through line 834 or the voltage on line 822 drops, the voltage on line 834 changes thus increasing the input to amplifier 840. The output of amplifier 840 is accordingly reduced to increase the conduction of transistor 838. Accordingly, the voltage on line 841 is similarly reduced. When the voltage on line 841 falls below approximately 0.7 volts, transistor 843 ceases to conduct and the voltage on line 847 increases. This turns on transistor 845 which reduces the voltage on line 849. Consequently, a low voltage alarm connected to line 849 will be actuated.

Supply voltage circuit 95 also contains a tampering alarm which is activated in the event that switch 806 is opened by mistake. The tampering alarm comprises flip flop 852 which has its non-inverted output connected to transistor 854. When flip flop 852 is set, transistor 854 is turned on thus sending a ground signal through line 855 to an appropriate alarm. The set input of flip flop 852 is connected through line 856 and line 857 to capacitor 858. Capacitor 858 is connected to the collector of transistor 859. Also, line 857 is connected to ground through filter capacitor 860, resistor 861 and clamping diode 862. The collector of transistor 859 is also connected through resistor 863 to line 864. Line 864 is supplied with positive voltage from unregulated supply line 822 through diode 865 or from a 9 volt battery connected to terminal 866 through diode 867. Line 864 also provides positive bias voltage for flip flop 852. The base of transistor 859 is connected through a voltage divider to line 822. Line 857 is also connected to the cathode of diode 870, the anode of which is connected to the base of transistor 871. The base and collector of transistor 871 are connected through bias resistors to line 873 which is connected to unregulated supply line 822. The collector of transistor 871 is also connected through line 874 to the reset input of flip flop 852.

In operation, as long as unregulated supply voltage is provided on line 822, transistor 859 is held in a conducting state and bias voltage is supplied to flip flop 852 through line 864 and diode 865. If the unregulated supply voltage is removed, as when switch 806 is opened, diode 865 becomes non-conducting and diode 867 conducts voltage to line 864. The base voltage of transistor 859 is removed and the transistor becomes non-conducting. The battery voltage from terminal 866 through diode 867, line 864 and resistor 863 causes an increase in voltage at the collector of transistor 859. This voltage increase is differentiated by capacitor 858 which causes a positive spike to pass through line 856 to the set input of flip flop 852. Flip flop 852 is set and thus passes a positive signal from its non-inverted output to transistor 854. Transistor 854 becomes conducting and line 855 goes to ground. This signal may be sent to the microprocessor of the system or be used to actuate any appropriate alarm.

Line 856 and the set input of flip flop 852 are also connected to reset switch 97 through line 98. Clearly, depressing reset switch 97 after power has been interrupted has no effect. Such depression of switch 97 merely provides a ground signal to the set input of flip flop 852 and, through diode 870 to the base of transistor 871. However, since the bias voltage on line 873 has been removed, no signal is sent to the reset input of flip flop 852 through line 874. In order to reset flip flop 852, the supply voltage must be reestablished, as through closure of switch 806. Once bias voltage has been returned to transistor 871, if switch 97 is depressed, a ground signal through diode 870 to the base of transistor 871 causes that transistor to become non-conducting. Accordingly, line 874 goes high sending a positive signal to the reset input of flip flop 852 resetting the flip flop.

Clearly, if it is desired to turn the power off, reset switch 97 should be depressed at the same time as switch 806 is opened. This causes the set pulse on line 856 to be shunted directly to ground and flip flop 852 never is set.

Figure 9:
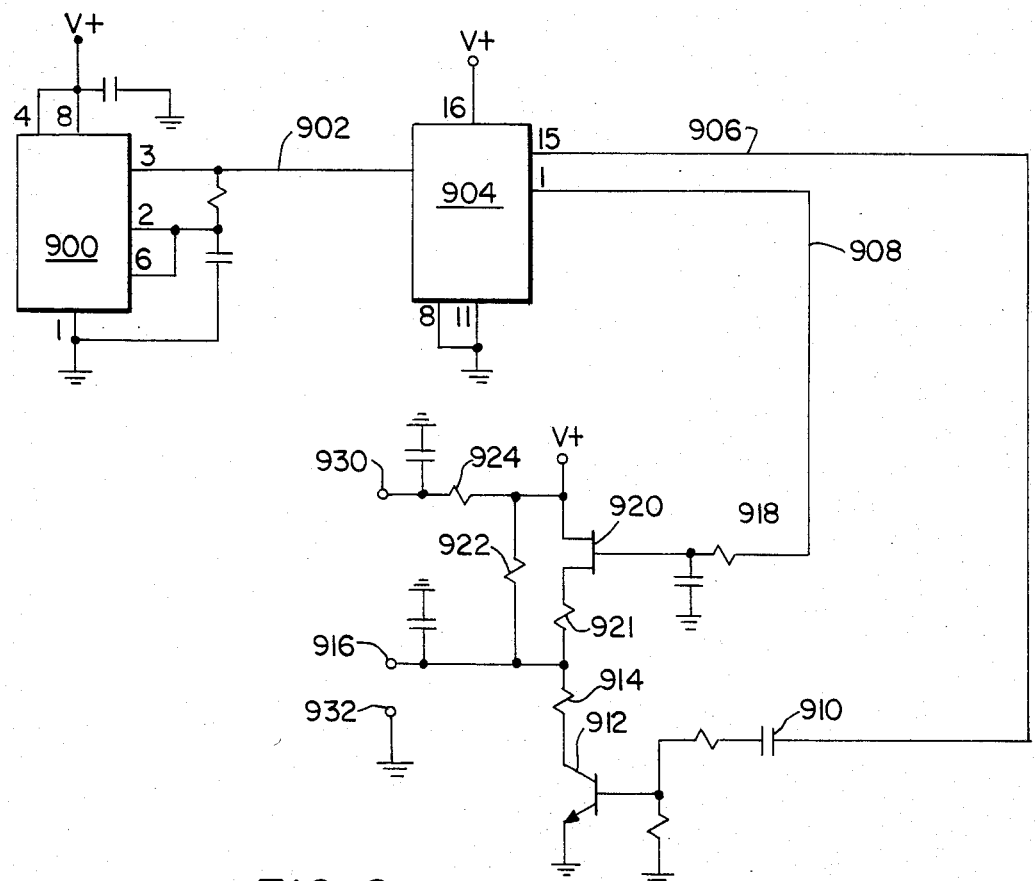
FIG. 9 is a schematic diagram of a test signal generation circuit for use with the present invention.

FIG. 9 shows a circuit which can be used to test the monitor of the present invention. The test circuit produces a 100 millisecond duration, 0.2 millivolt amplitude pulse at the rate of 154 per minute to simulate ECG. It also generates a 0.2 ohm amplitude, one second duration pulse at the rate of 77 per minute to simulate thoracic impedance variation due to respiration.

The circuit comprises an integrated circuit oscillator 900 which can be an Intersil ICM 7555 oscillator biased to generate pulses at a multiple of 154 per minute. The output of oscillator 900 is passed through line 902 to counter circuit 904. Counter 904 can be a Motorola Model MC14040 counter. Two outputs from counter 904 are provided on lines 906 and 908. The output on line 906 is at a frequency twice that of the output on line 908. The frequency of the output on line 906 should be 154 pulses per minute, and the output on line 908 should be 77 pulses per minute. Line 906 is connected to capacitor 910 which differentiates the pulses and provides spikes to the base of transistor 912 through a voltage divider network. The output of transistor 912 is taken from its collector through resistor 914 which may be a 200K ohm resistor. Accordingly, it can be seen that the output of transistor 912 comprises a plurality of spikes which are similar to the R wave portion of an ECG wave. These spikes are passed through resistor 914 to line 916 at a rate of 154 per minute.

Line 908 is connected through resistor 918 to the gate of FET 920. A 499 ohm resistor 921 is connected between the drain of FET 920 and line 916. A 10 ohm resistor 922 is connected from the source of FET 920 to line 916. A 100 ohm resistor 924 is connected between the source of FET 920 and output terminal 930. Accordingly, it will be seen that FET 920 will be turned on at a rate of 77 times per minute in accordance with the pulses received from line 908. Each time FET 920 is turned on, resistor 921 is placed in parallel with resistor 922 thereby bringing the combined resistance to a total slightly less than 10 ohms. This resistance change is approximately equal to 0.2 ohms. Consequently, it can be seen that the resistance variation between lines 916 and 930 will be approximately 0.2 ohms at a rate of 77 times per minute.

It will be understood that lines 930 and 916 will be connected to the input of circuit 14 in place of the patient connected leads and ground lead 932 should be connected to the ground of circuit 14. In this manner, simulated respiration and ECG waves will be processed by the monitor of the present invention. Outputs from the monitor 10 can be observed to determine whether the system is operating properly.

The foregoing description is set forth for the purpose of illustrating the invention but is not meant to limit the scope thereof in any way. Clearly numerous modifications, additions, and other changes can be made to the present invention without departing from the scope thereof as set forth in the appended claims.

We claim:

1. A patient monitor comprising:
   a patient unit comprising:
      a probe connected to receive a carrier signal, said probe being adapted for connection to the body of a patient to be monitored, whereby said carrier signal is modulated in accordance with respirations of said patient to produce a modulated carrier signal;
      carrier detection means connected to receive said modulated carrier signal and produce a demodulated respiration signal;
      first baseline correction circuit means for altering the D.C. level of said demodulated respiration signal, said first baseline correction circuit means including means for sensing a variation in the level of said carrier signal and adjusting the DC level of said demodulated respiration signal in response to said variation; and
      modulation means for receiving and modulating said demodulated respiration signal to produce a second modulated respiration signal; and
   an analysis unit comprising:
      carrier generation means for producing said carrier signal;
      a demodulation circuit for receiving said second modulated respiration signal and demodulating said second modulated respiration signal thereby producing a respiration data signal;
      an output circuit connected to receive said respiration data signal, amplify and level shift said respiration data signal, and output said respiration data signal;
      isolation means for electrically isolating said patient unit from said analysis unit, said isolation means providing communication links for passing said carrier signal to said patient unit and said second modulated respiration signal to said analysis unit; and
      a baseline reset circuit including level sensing means for sensing the DC level of said respiration data signal and causing said variation in the level of said carrier signal when said DC level of said respiration data signal reaches a predetermined level.

2. The monitor as set forth in claim 1, wherein said first baseline correction circuit means includes respiration baseline correction circuit means for sensing the DC level of said demodulated respiration signal and adding or subtracting a DC signal with said demodulated respiration signal in response to said sensed DC level.

3. The monitor as set forth in claim 2, wherein said respiration baseline correction circuit means includes a capacitor which is charged in response to said sensed DC level.

4. The monitor as set forth in claim 3, wherein said sensing means is operative for discharging said capacitor in response to said variation of said carrier signal.

5. The monitor as set forth in claim 4, wherein said baseline reset circuit includes means for deactivating said carrier generation means to stop the production of said carrier signal, and said sensing means senses the lack of carrier signal and discharges said capacitor in response thereto.

6. The monitor as set forth in claim 1 and further including a baseline correction circuit means in said analysis unit for sensing the DC level of said respiration data signal and adding or subtracting a DC signal to said respiration data signal in response to said sensed DC level.

7. The monitor as set forth in claim 6, wherein said analysis unit baseline correction circuit means contains an integrator whose output changes with said sensed DC level.

8. The monitor as set forth in claim 7 and further including means for varying the rate of charging said integrator.

9. The monitor as set forth in claim 8, wherein said varying means includes means for rapidly decreasing a time constant of said integrator when the DC level of said respiration data signal is above or below predetermined limits.

10. The monitor as set forth in claim 9, wherein said rapid time constant decreasing means includes a programmed microprocessor.

11. The monitor as set forth in claim 9, wherein said rapid time constant decreasing means includes a pair of differential comparator circuits connected to receive said respiration data signal and produce output signals when said respiration data signal is above or below upper and lower limits, respectively.

12. The monitor as set forth in claim 8, wherein said varying means includes means for increasing a time constant of said integrator.

13. The monitor as set forth in claim 8 and further wherein said analysis unit includes a switch for connecting said frequency demodulation circuit to said output circuit when closed and disconnecting said frequency demodulation circuit from said output circuit when open, and wherein said rapidly varying means is operative for opening said switch when said DC level of said respiration data signal is above or below said predetermined limits.

14. The monitor as set forth in claim 1 and further wherein said patient unit includes a loose lead detector means for sensing the presence of said demodulated respiration signal and deactivating said frequency modulation means when no demodulated signal is present.

15. The monitor as set forth in claim 14 and further wherein said analysis unit includes a loose lead detector for sensing the presence of said respiration data signal and producing an output signal when no respiration data signal is present.

16. The monitor as set forth in claim 1 and further wherein said carrier detection means comprises a synchronous detector.

17. The monitor as set forth in claim 16, wherein said carrier detection means further includes a low pass filter connected to the output of said synchronous detector to pass frequencies below said carrier signal frequency.

18. The monitor as set forth in claim 1 and further including an ECG sensing circuit connected to said probe for sensing ECG signals produced by said patient.

19. The monitor as set forth in claim 18, wherein said ECG sensing circuit includes a filter contained in said patient unit for passing frequencies associated with an ECG signal.

20. The monitor as set forth in claim 19 and further including ECG amplifier means for amplifying said frequencies passed by said filter to produce an amplified ECG signal, and ECG modulation means connected to modulate said amplified ECG signal to produce a modulated ECG signal, said ECG amplifier means and said ECG modulation means being contained in said patient unit, and an ECG demodulation circuit contained in said analysis unit for demodulating said modulated ECG signal to produce an ECG data signal, and an ECG output circuit contained in said analysis unit for receiving said ECG data signal, amplify, level shift and output said ECG data signal.

21. The monitor as set forth in claim 20, wherein said ECG output circuit further includes an automatic gain control circuit for controlling the amplitude of said ECG data signal to be within predetermined limits.

22. The monitor as set forth in claim 21, wherein said automatic gain control circuit includes a gain controllable amplifier, and a gain control circuit connected to receive the output of said gain controllable amplifier and increase or decrease the gain thereof in response to said received output thereof.

23. The monitor as set forth in claim 22, wherein said gain controllable amplifier includes a variable resistance optical coupler contained in a feedback path, and said gain control circuit being connected to increase or decrease the resistance of said optical coupler in response to the received output of said gain controllable amplifier.

24. The monitor as set forth in claim 23, wherein said gain control circuit includes an integrator circuit having an input connected to receive said output from said gain controllable amplifier, and an output connected to said optical coupler.

25. The monitor as set forth in claim 20, wherein said isolation means also comprises a communication link for passing said modulated ECG signal to said analysis unit.

26. The monitor as set forth in claim 20 and further including an ECG baseline correction circuit means for sensing the DC level of said amplified ECG signal and adding or subtracting a DC signal to said amplified ECG signal in response to said sensed DC level.

27. The monitor as set forth in claim 26, wherein said ECG baseline correction circuit means includes a capacitor which is charged in accordance with said sensed DC level.

28. The monitor as set forth in claim 27, wherein said first baseline correction circuit means includes respiration baseline correction circuit means for sensing the DC level of said demodulated respiration signal and adding or subtracting a DC signal with said demodulated respiration signal in response to said sensed DC level.

29. The monitor as set forth in claim 28, wherein said respiration baseline correction circuit means includes a capacitor which is charged in accordance with said sensed DC level.

30. The monitor as set forth in claim 29, wherein said sensing means is operative for discharging said capacitors in said ECG and respiration baseline correction circuit means in response to said variation in the level of said carrier signal and wherein said baseline reset circuit causes said variation both in response to the DC level of said respiration data signal reaching a predetermined amount, and in response to the DC level of said ECG data signal reaching a predetermined amount.

31. The monitor as set forth in claim 30, wherein said baseline reset circuit comprises means for deactivating said carrier generation means to stop the production of said carrier signal, and said sensing means senses the lack of carrier signal and discharges said capacitors in response thereto.

32. The monitor as set forth in claim 20 and further including an ECG baseline correction circuit means in said analysis unit for sensing the DC level of said ECG data signal and adding or subtracting a DC signal to said ECG data signal in response to said sensed DC level.

33. The monitor as set forth in claim 32, wherein said analysis unit ECG baseline correction circuit means includes an integrator whose output changes with said sensed DC level of said ECG data signal.

34. The monitor as set forth in claim 33 and further including means for varying the rate of charging of said integrator.

35. The monitor as set forth in claim 34, wherein said varying means includes means for rapidly decreasing a time constant of said integrator when the DC level of said ECG data signal is above or below predetermined limits.

36. The monitor as set forth in claim 34, wherein said rapid time constant decreasing means includes a programmed microprocessor.

37. The monitor as set forth in claim 35, wherein said rapid time constant decreasing means includes a pair of differential comparator circuits connected to receive said ECG data signal and produce output signals when the ECG data signal is above or below upper and lower limits, respectively.

38. A patient monitor comprising:
carrier generation means for producing a carrier signal;
a probe connected to receive said carrier signal, said probe being adapted for connection to a patient to be monitored, whereby said carrier signal is modulated in accordance with respirations of said patient to produce a modulated carrier signal;
carrier detection means connected to receive said modulated carrier signal and produce a demodulated respiration signal;
amplifier means for amplifying said demodulated respiration signal and outputting an amplified respiration signal;
an ECG filter connected to receive an ECG signal produced by said patient and filter said ECG signal from said carrier signal;
ECG amplifying means for receiving said ECG signal, and amplifying and outputting said ECG signal;
respiration baseline correction circuit means for sensing the DC level of said respiration signal and adding or subtracting a DC signal to said respiration signal in response to said sensed DC level;
ECG baseline correction circuit means for sensing the DC level of said ECG signal and adding or subtracting a DC signal to said ECG signal in response to the sensed DC level thereof; and
a baseline reset circuit including level sensing means for sensing the DC level of said respiration signal and the DC level of said ECG signal and deactuating said carrier generation means when either of said DC levels becomes excessive, and control means for sensing the deactuation of said carrier generation means and controlling both the ECG baseline and the respiration baseline to return to an original condition.

39. A patient monitor according to claim 18 or 38 and further including a logarithmic compression circuit having an input connected to receive said respiration signal and an output for providing a signal which is proportional to the logarithm of said received respiration signal in order to reduce the dynamic range of said respiration signal.

40. The patient monitor as set forth in claim 39, wherein said logarithmic compression circuit includes an operational amplifier and a plurality of diodes connected in a feedback network on said operational amplifier.

41. The patient monitor as set forth in claim 1 or 38 and further including an actuatable reset switch and a power supply which can be turned on or off, and alarm circuit means for producing an alarm signal when said power supply is turned off if said reset switch is not actuated.

42. The patient monitor as set forth in claim 41, wherein said alarm circuit means further includes inhibit circuit means for eliminating said alarm signal only when said power supply is turned on and said reset switch is actuated.

43. The patient monitor as set forth in claim 41, wherein said power supply further includes low voltage alarm circuit means for producing an alarm signal when the output of said power supply falls below a predetermined limit.

44. The patient monitor as set forth in claim 41, wherein said alarm circuit means includes means for inhibiting said alarm signal if said reset switch is actuated when said power supply is turned off.

45. The patient monitor as set forth in claim 1 or 38 and further in combination with a test signal generation means for producing a simulated respiration wave form, said test signal generation means having output terminals for connection to said patient unit.

46. The combination as set forth in claim 45, wherein said test signal generation means comprises an oscillator, a fixed resistance, and a semiconductor component having an input connected to an output of said oscillator and having output terminals connected across said fixed resistance.

47. The patient monitor as set forth in claims 18 or 38 and further including a test signal generation circuit means for producing simulated ECG and respiration wave forms, said test signal generation means having outputs for connection to said patient monitor.

48. The combination as set forth in claim 47, wherein said test signal generation means comprises an oscillator, a counter connected to said oscillator, said counter having a first output providing pulses at a first frequency and a second output for providing pulses at a second frequency, means for differentiating signals received from one of said outputs, and semiconductor means actuated by said differentiated signals, and variable resistance means connected and responsive thereto to produce a variation in resistance.

49. The monitor as set forth in claim 1, further including means in said patient unit for rectifying said carrier signal and supplying said rectified carrier signal as a bias voltage for said patient unit.

50. The monitor as set forth in claim 1, wherein said modulation means is a pulse width modulator.

51. The monitor as set forth in claim 20, wherein said ECG modulator means is a pulse width modulator.

52. In combination:
a first circuit connected to a power source, said first circuit including means for generating an alternating signal, means for detecting a baseline deviation of an information bearing signal, and means for adjusting the level of said alternating signal in response to said baseline deviation, and a second circuit electrically isolated from said first circuit, said second circuit including means for receiving said alternating signal from said first circuit, and rectifying said received alternating signal to provide bias voltage for said second circuit, means for providing said information bearing signal to said first circuit, and means for sensing said deviation in said alternating signal and adjusting a baseline of said information bearing signal in response to said sensed deviation;

wherein said first circuit receives said information bearing signal and adjusts the level of said alternating signal in response to a detected baseline deviation of said information bearing signal.

* * * * *